US008865645B2

(12) United States Patent
Amatucci et al.

(10) Patent No.: US 8,865,645 B2
(45) Date of Patent: Oct. 21, 2014

(54) METHOD OF TREATING LUNG FIBROSIS USING ST2 POLYPEPTIDE

(75) Inventors: Aldo Amatucci, Winthrop, MA (US); Tatiana Novobrantseva, Wellesley, MA (US); Alexander Ibraghimov, Southborough, MA (US); Alan Gill, Reading, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 1363 days.

(21) Appl. No.: 12/301,736

(22) PCT Filed: May 23, 2007

(86) PCT No.: PCT/US2007/069538

§ 371 (c)(1),
(2), (4) Date: May 28, 2009

(87) PCT Pub. No.: WO2007/140205

PCT Pub. Date: Dec. 6, 2007

(65) Prior Publication Data

US 2009/0304699 A1    Dec. 10, 2009

Related U.S. Application Data

(60) Provisional application No. 60/802,903, filed on May 24, 2006.

(51) Int. Cl.
*A61K 38/00* (2006.01)
*A61K 38/17* (2006.01)

(52) U.S. Cl.
CPC ......... *A61K 38/1793* (2013.01); *C07K 2319/30* (2013.01)
USPC .......................................................... 514/2

(58) Field of Classification Search
CPC ................... G01N 33/68689; G01N 2800/32; G01N 33/6893; C12Q 1/6883; C12Q 2600/158
See application file for complete search history.

(56) References Cited

PUBLICATIONS

Tajima et al. (Chest 2003, 124:1206-1214).*
Leung et al. (J. Immunol. 2004, 173:145-150).*
Attwood (Science 290: 471-473, 2000).*
Skolnick et al. (Trends in Biotech. 18: 34-39, 2000).*
Amatucci et al., "Recombinant ST2 Boosts hepatic Th2 response in vivo," J. Leukocyte Biology, 82:124-132 (2007).
International Search Report for PCT/US2007/069538, mailed Aug. 26, 2008 from the International Searching Authority of the United States.
Oshikawa et al., "Elevated Soluble ST2 Protein Levels in Sera of Patients with Asthma with an Acute Exacerbation," Am J Respir Crit Care Med, 164:277-281 (2001).
Tajima et al., "The Increase in Serum Soluble ST2 Protein Upon Acute Exacerbation of Idiopathic Pulmonary Fibrosis," Clinical Investigations, 124:1206-1214 (2003).
Bergers et al. (1994) "Alternative promoter usage of the Fos-responsive gene *Fit-1* generates mRNA isoforms coding for either secreted or membrane-bound proteins related to the IL-1 receptor" *Embo J.* 13:1176-1188.
Brint et al. (2004) "ST2 is an inhibitor of interleukin 1 receptor and Toll-like receptor 4 signaling and maintains endotoxin tolerance" *Nat. Immunol.* 5:373-379.
Carter et al. (2001) "Regulation of ST2L expression on T helper (Th) type 2 cells" *Eur. J. Immunol.* 31:2979-2985.
Chan et al. (2001) "Human IL-18 receptor and ST2L are stable and selective markers for the respective type 1 and type 2 circulating lymphocytes" *J. Immunol.* 167:1238-1244.
Coyle et al. (1999) "Crucial Role of the Interleukin 1 Receptor Family Member T1/ST2 in T Helper Cell Type 2-mediated Lung Mucosal Immune Responses" *J. Exp. Med.* 190:895-902.
Gächter et al. (1996) "Transcription of the Interleukin-1 Receptor-related T1 Gene is Initiated at Different Promoters in Mast Cells and Fibroblasts" *J. Biol. Chem.* 271:124-129.
Gajewska et al. (2001) "Temporal-Spatial Analysis of the Immune Response in a Murine Model of Ovalbumin-Induced Airways Inflammation" *Am. J. Respir. Cell Mol. Biol.* 25:326-334.
Iwahana et al. (2004) "Molecular cloning of the chicken ST2 gene and a novel variant form of the ST2 gene product, ST2LV" *Biochim. Biophys. Acta* 1681:1-14.
Johnson et al. (2004) "Continuous Exposure to House Dust Mite Elicits Chronic Airway Inflammation and Structural Remodeling" *Am. J Respir. Crit. Care Med.* 169:378-385.
Kropf et al. (2003) "Signaling through the T1/ST2 Molecule is Not Necessary for Th2 Differentiation but is Important for the Regulation of Type 1 Responses in Nonhealing *Leishmania major* Infection" *Infection and Immunity* 71:1961-1971.
Lambrecht et al. (2000) "Myeloid dendritic cells induce Th2 responses to inhaled antigen, leading to eosinophilic airway inflammation" *J. Clin. Invest.* 106:551-559.
Lécart et al. (2001) "Phenotypic Characterization of Human CD4+ Regulatory T Cells Obtained from Cutaneous Dinitrochlorobenzene-Induced Delayed Type Hypersensitivity Reactions" *J. Invest. Dermatol.* 117: 318-325.
Lécart et al. (2002) "Activated, but not resting human Th2 cells, in contrast to Th1 and T regulatory cells, produce soluble ST2 and express low levels of ST2L at the cell surface" *Eur. J. Immunol.* 32: 2979-2987.
Löhning et al. (1998) "T1/ST2 is preferentially expressed on murine Th2 cells, independent of interleukin 4, interleukin 5, and interleukin 10, and important for Th2 effector function" *Proc. Natl. Acad. Sci. USA* 95:6930-6935.
McGuirk et al. (2002) "Pathogen-specific T Regulatory 1 Cells Induced in the Respiratory Tract by a Bacterial Molecule that Stimulates Interleukin 10 Production by Dendritic Cells: A Novel Strategy for Evasion of Protective T Helper Type 1 Responses by *Bordetella pertussis*" *J. Exp. Med.* 195:221-231.
Meisel et al. (2001) "Regulation and Function of T1/ST2 Expression on CD4+T Cells: Induction of Type 2 Cytokine Production by T1/ST2 Cross-Linking" *J Immunol.* 166:3143-3150.
Oshikawa et al. (2002) "Expression and function of the ST2 gene in a murine model of allergic airway inflammation" *Clin. Exp. Allergy* 32:1520-1526.

(Continued)

*Primary Examiner* — Sharon Wen
(74) *Attorney, Agent, or Firm* — Fish & Richardson P.C.

(57) ABSTRACT

Methods and compositions for treating fibrosis are disclosed.

11 Claims, 10 Drawing Sheets

(56) References Cited

PUBLICATIONS

Oshikawa et al. (2002) "ST2 protein induced by inflammatory stimuli can modulate acute lung inflammation" *Biochem. Biophys. Res. Commun.* 299:18-24.

Saccani et al. (1998) "Divergent effects of LPS on expression of IL-1 receptor family members in mononuclear phagocytes in vitro and in vivo" *Cytokine* 10:773-779.

Schmitz et al. (2005) "IL-33, an Interleukin-1-like Cytokine that Signals via the IL-1 Receptor-Related Protein ST2 and Induces T Helper Type 2-Associated Cytokines" *Immunity* 23:479-490.

Senn et al. (2000) "T1-deficient and T1-Fc-transgenic mice develop a normal protective Th2-type immune response following infection with *Nippostrongylus brasiliensis*" *Eur. J Immunol.* 30:1929-1938.

Shuey (2002) "RNAi: gene-silencing in therapeutic intervention" *Drug Discov Today* 7:1040-1046.

Sweet et al. (2001) "A Novel Pathway Regulating Lipopolysaccharide-Induced Shock by ST2/T1 Via Inhibition of Toll-Like Receptor 4 Expression" *J. Immunol.* 166:6633-6639.

Tominaga et al. (1991) "Molecular cloning of the murine ST2 gene. Characterization and chromosomal mapping" *Biochim. Biophys. Acta* 1090:1-8.

Tominaga et al. (1992) "Nucleotide sequence of a complementary DNA for human ST2" *Biochim. Biophys. Acta* 1171:215-218.

Townsend et al. (2000) "T1/ST2-deficient Mice Demonstrate the Importance of T1/ST2 in Developing Primary T Helper Cell Type 2 Responses" *J. Exp. Med.* 191:1069-1075.

Walzl et al. (2001) "Inhibition of T1/ST2 during Respiratory Syncytial Virus Infection Prevents T Helper Cell Type 2 (Th2)- but not Th1-driven Immunopathology" *J. Exp. Med.* 193:785-792.

Written Opinion issued in International Patent Application No. PCT/US2007/069538, mailed Aug. 26, 2008.

Xu et al. (1998) "Selective Expression of a Stable Cell Surface Molecule on Type 2 but Not Type 1 Helper T Cells" *J. Exp. Med.* 187:787-794.

\* cited by examiner

A.
MIDRQRMGLWALAILTLPMYLTVTEGSKSSWGLENEALIVRCPQRGRSTYPVEWYYSDTNESIPTQKRNRIF
VSRDRLKFLPARVEDSGIYACVIRSPNLNKTGYLNVTIHKKPPSCNIPDYLMYSTVRGSDKNFKITCPTIDL
YNWTAPVQWFKNCKALQEPRFRAHRSYLFIDNVTHDDEGDYTCQFTHAENGTNYIVTATRSFTVEEKGFSMF
PVITNPPYNHTMEVEIGKPASIACSACFGKGSHFLADVLWQINKTVGNFGEARIQEEEGRNESSSNDMDCL
TSVLRITGVTEKDLSLEYDCLALNLHGMIRHTIRLRRKQPIDHRSIYYVDPRGPTIKPCPPCKCPAPNLLGG
PSVFIFPPKIKDVLMISLSPIVTCVVVDVSEDDPDVQISWFVNNVEVHTAQTQTHREDYNSTLRVVSALPIQ
HQDWMSGKEFKCKVNNKDLPAPIERTISKPKGSVRAPQVYVLPPPEEEMTKKQVTLTCMVTDFMPEDIYVEW
TNNGKTELNYKNTEPVLDSDGSYFMYSKLRVEKKNWVERNSYSCSVVHEGLHNHHTTKSFSRTPGK

FIG. 12A

B.
atgattgacagagacagagaatgggactttgggctttggcatttgacacattccatgtatttgacagttacggagggcagtaaatcgtcctgsggtctggaaatgaggctttaatt
gtgagatgcccccaaagagagacgctcgacttatcctgtggaatggtattactcagatacaaatgaaagtattcctactcaaaaagaaatcggatcttttctcaagagatcgtctg
aagttctaccagccagagccagagtggaagactctggatttatgcttgttgtatcagaagacccccaacttgaataagactggatacttgaatgtcaccatacataaaaagcccaagctg
caatatcccctgattattgatgtactgacagatcgacgcggatcagatataaaaatttcaagatacgtccaacaattgacactgtataattggacagcaccttcagtggtttaagraact
gcaaagctctccaagagccaaggttcaggggcacacaggtcctactgttcattgacaacgtgactcatgatgatgaaggtgactacacttgtcaatttcacacacgcggagaatg
gaaccaactacatcgtgacgggccaccagatcattcacagttgaagaaaaaaggcttttctatgtttccagtaattacaaatcttccataacaaccacaatagaaagtggaaatagga
aaaccagcaagtattgcctgttcagcttgcttttggcaaaaggctctcacttcttgctgatgtcctgtgcagattaacaaaacagtagttgaaatttggtgaaagcaagaaattcaag
aagaggaagtcgaaatgaaaggtcacacataaggcacaccataaaggctgagaaggaaaacaaccaattgatcaccgaagcatctactgtcacCCCAGAGGGCCACAATCA
gaaccttcatggcatgataaggcactagataaggctgagaaggaaaacaaccaattgatcaccgaagcatctactgtcacCCCAGAGGGCCACAATCA
AGCCCTGTCCTCCATGCAAATGCCCAGCACCTAACCTCTTGGGTGGACCATCCGTCTTCATCTTCCCTCCA
AAGATCAAGGATGTACTCATGATCTCCCTGAGCCCCATAGTCACATGTCACATGTGTGGTGGATGTGAGGGAGG
ATGACCCAGAGATGTCCCAGATCAGCTGGTTTGTGAACGTGGAAGTACACACAGCTCAGACACAAACCCA
TAGAGAGGATTACAACAGTACACTCTCCGGGTGGTCAGTGCCCTCCCCATCCAGCACCAGGACTGGATGAGT
GGCAAGGAGTTCAAATGCAAGGTCAACAACAAAGACCTCCCAGCGCCCATCGAGAGAAGAACCATCTCAAA
CCCAAAGGGTCAGTAAGAGCCTGCATGGTGACCCACAGGTATATGTCTTGCCTGAAGACATTTACGTGGAGACTAAGAAAC
AGGTCACTCTGACCTGCCATGGTGACAGAACACTGAAACCAGTCCTGGAACTCTGATGTTCTTACTTCATGTACAGC
GAAAACAGAGTCAAACTACAAGAAGAACTGGGGTGAAAGAAATAGCTACTCCCTGTTCATGGTCCACGAGGGTC
AAGCTGAGAGTGGAAAAGAAGAACTAAGAGAGCTTCTCCCGGACTCCGGGTAAA
TGCACAATCACCACACGACTAAGAGAGCTTCTCCCGGACTCCGGGTAAA

FIG. 12B

SEQUENCE LISTING

```
<160> NUMBER OF SEQ ID NOS: 2

<210> SEQ ID NO 1
<211> LENGTH: 1709
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atgattgaca gacagagaat gggactttgg gctttggcaa ttctgacact tcccatgtat      60
ttgacagtta cggagggcag taaatcgtcc tggggtctgg aaaatgaggc tttaattgtg     120
agatgccccc aaagaggacg ctcgacttat cctgtggaat ggtattactc agatacaaat     180
gaaagtattc ctactcaaaa aagaaatcgg atctttgtct caagagatcg tctgaagttt     240
ctaccagcca gagtggaaga ctctgggatt tatgcttgtg ttatcagaag ccccaacttg     300
aataagactg gatacttgaa tgtcaccata cataaaaagc cgccaagctg caatatccct     360
gattatttga tgtactcgac agtacgcgga tcagataaaa atttcaagat aacgtgtcca     420
acaattgacc tgtataattg gacagcacct gttcagtggt ttaagaactg caaagctctc     480
caagagccaa ggttcagggc acacaggtcc tacttgttca ttgacaacgt gactcatgat     540
gatgaaggtg actacacttg tcaattcaca cacgcggaga atggaaccaa ctacatcgtg     600
acggccacca tcattcac agttgaagaa aaaggctttt ctatgtttcc agtaattaca     660
```

```
aatcctccat acaaccacac aatggaagtg gaaataggaa aaccagcaag tattgcctgt      720
tcagcttgct ttggcaaagg ctctcacttc ttggctgatg tcctgtggca gattaacaaa      780
acagtagttg gaaattttgg tgaagcaaga attcaagaag aggaaggtcg aaatgaaagt      840
tccagcaatg acatggattg tttaacctca gtgttaagga taactggtgt gacagaaaag      900
gacctgtccc tggaatatga ctgtctggcc ctgaaccttc atggcatgat aaggcacacc      960
ataaggctga aaggaaaaca accaattgat caccgaagca tctactacgt cgaccccaga     1020
gggcccacaa tcaagccctg tcctccatgc aaatgcccag cacctaacct cttgggtgga     1080
ccatccgtct tcatcttccc tccaaagatc aaggatgtac tcatgatctc cctgagcccc     1140
atagtcacat gtgtggtggt ggatgtgagc gaggatgacc cagatgtcca gatcagctgg     1200
tttgtgaaca acgtggaagt acacacagct cagacacaaa cccatagaga ggattacaac     1260
agtactctcc gggtggtcag tgccctcccc atccagcacc aggactggat gagtggcaag     1320
gagttcaaat gcaaggtcaa caacaaagac ctcccagcgc ccatcgagag aaccatctca     1380
aaacccaaag ggtcagtaag agctccacag gtatatgtct tgcctccacc agaagaagag     1440
atgactaaga aacaggtcac tctgacctgc atggtgacag acttcatgcc tgaagacatt     1500
tacgtggagt ggaccaacaa cgggaaaaca gagctaaact acaagaacac tgaaccagtc     1560
ctggactctg atggttctta cttcatgtac agcaagctga gagtgaaaaa gaagaactgg     1620
gtggaaagaa atagctactc ctgttcatgg tccacgaggg tctgcacaat caccacacga     1680
ctaagagctt ctcccggact ccgggtaaa                                       1709
```

<210> SEQ ID NO 2
<211> LENGTH: 570
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ile Asp Arg Gln Arg Met Gly Leu Trp Ala Leu Ala Ile Leu Thr
1               5                   10                  15

Leu Pro Met Tyr Leu Thr Val Thr Glu Gly Ser Lys Ser Ser Trp Gly
                20                  25                  30

Leu Glu Asn Glu Ala Leu Ile Val Arg Cys Pro Gln Arg Gly Arg Ser
            35                  40                  45

Thr Tyr Pro Val Glu Trp Tyr Tyr Ser Asp Thr Asn Glu Ser Ile Pro
        50                  55                  60

Thr Gln Lys Arg Asn Arg Ile Phe Val Ser Arg Asp Arg Leu Lys Phe
65                  70                  75                  80

Leu Pro Ala Arg Val Glu Asp Ser Gly Ile Tyr Ala Cys Val Ile Arg
                85                  90                  95

Ser Pro Asn Leu Asn Lys Thr Gly Tyr Leu Asn Val Thr Ile His Lys
            100                 105                 110

Lys Pro Pro Ser Cys Asn Ile Pro Asp Tyr Leu Met Tyr Ser Thr Val
        115                 120                 125

Arg Gly Ser Asp Lys Asn Phe Lys Ile Thr Cys Pro Thr Ile Asp Leu
    130                 135                 140

Tyr Asn Trp Thr Ala Pro Val Gln Trp Phe Lys Asn Cys Lys Ala Leu
145                 150                 155                 160

Gln Glu Pro Arg Phe Arg Ala His Arg Ser Tyr Leu Phe Ile Asp Asn

```
                    165                 170                 175
Val Thr His Asp Asp Glu Gly Asp Tyr Thr Cys Gln Phe Thr His Ala
                180                 185                 190
Glu Asn Gly Thr Asn Tyr Ile Val Thr Ala Thr Arg Ser Phe Thr Val
            195                 200                 205
Glu Glu Lys Gly Phe Ser Met Phe Pro Val Ile Thr Asn Pro Pro Tyr
210                 215                 220
Asn His Thr Met Glu Val Glu Ile Gly Lys Pro Ala Ser Ile Ala Cys
225                 230                 235                 240
Ser Ala Cys Phe Gly Lys Gly Ser His Phe Leu Ala Asp Val Leu Trp
                245                 250                 255
Gln Ile Asn Lys Thr Val Val Gly Asn Phe Gly Glu Ala Arg Ile Gln
            260                 265                 270
Glu Glu Glu Gly Arg Asn Glu Ser Ser Asn Asp Met Asp Cys Leu
        275                 280                 285
Thr Ser Val Leu Arg Ile Thr Gly Val Thr Glu Lys Asp Leu Ser Leu
    290                 295                 300
Glu Tyr Asp Cys Leu Ala Leu Asn Leu His Gly Met Ile Arg His Thr
305                 310                 315                 320
Ile Arg Leu Arg Arg Lys Gln Pro Ile Asp His Arg Ser Ile Tyr Tyr
                325                 330                 335
Val Asp Pro Arg Gly Pro Thr Ile Lys Pro Cys Pro Pro Cys Lys Cys
            340                 345                 350
Pro Ala Pro Asn Leu Leu Gly Gly Pro Ser Val Phe Ile Phe Pro Pro
        355                 360                 365
Lys Ile Lys Asp Val Leu Met Ile Ser Leu Ser Pro Ile Val Thr Cys
    370                 375                 380
Val Val Val Asp Val Ser Glu Asp Asp Pro Asp Val Gln Ile Ser Trp
385                 390                 395                 400
Phe Val Asn Asn Val Glu Val His Thr Ala Gln Thr Gln Thr His Arg
                405                 410                 415
Glu Asp Tyr Asn Ser Thr Leu Arg Val Val Ser Ala Leu Pro Ile Gln
            420                 425                 430
His Gln Asp Trp Met Ser Gly Lys Glu Phe Lys Cys Lys Val Asn Asn
        435                 440                 445
Lys Asp Leu Pro Ala Pro Ile Glu Arg Thr Ile Ser Lys Pro Lys Gly
    450                 455                 460
Ser Val Arg Ala Pro Gln Val Tyr Val Leu Pro Pro Pro Glu Glu Glu
465                 470                 475                 480
Met Thr Lys Lys Gln Val Thr Leu Thr Cys Met Val Thr Asp Phe Met
                485                 490                 495
Pro Glu Asp Ile Tyr Val Glu Trp Thr Asn Asn Gly Lys Thr Glu Leu
            500                 505                 510
Asn Tyr Lys Asn Thr Glu Pro Val Leu Asp Ser Asp Gly Ser Tyr Phe
        515                 520                 525
Met Tyr Ser Lys Leu Arg Val Glu Lys Lys Asn Trp Val Glu Arg Asn
    530                 535                 540
Ser Tyr Ser Cys Ser Val Val His Glu Gly Leu His Asn His His Thr
545                 550                 555                 560
Thr Lys Ser Phe Ser Arg Thr Pro Gly Lys
                565                 570
```

METHOD OF TREATING LUNG FIBROSIS USING ST2 POLYPEPTIDE

CROSS-REFERENCE TO RELATED APPLICATIONS

This application is a national stage entry under 35 U.S.C. §371 of International Application No. PCT/US2007/069538, filed May 23, 2007, which claims the benefit under 35 U.S.C. §119(e) of U.S. Provisional Application No. 60/802,903, filed May 24, 2006, both of which are hereby incorporated by reference in their entirety.

BACKGROUND

Tissue fibrosis is a pathologic process characterized by the abnormal accumulation of extracellular matrix in the interstitium ultimately resulting in loss of function.

SUMMARY

The invention is based, in part, on the observation that modulation of ST2 can be used to treat fibrosis. Accordingly, in one aspect, the invention provides methods of treating lung fibrosis in a subject. The method includes administering to the subject an ST2-modulating agent, e.g., an agent that binds a naturally-occurring ST2 ligand, e.g., an agent that binds IL33, in an amount effective to treat lung fibrosis. While not wishing to be bound by theory, such agents may act by disrupting an interaction between ST2, e.g., ST2L, and a naturally occurring ligand, e.g., IL33.

Preferred agents include soluble ST2 polypeptides, including ST2 fusion proteins. In some embodiments, the soluble ST2 polypeptide lacks a sufficient portion of its membrane-spanning domain to anchor the polypeptide or is modified such that the membrane-spanning domain is non-functional. In some embodiments, the soluble ST2 polypeptide includes the entire extracellular sequence. An exemplary soluble ST2 polypeptide includes amino acids 1-336 depicted in FIG. 12A (SEQ ID NO:2). This exemplary soluble ST2 polypeptide can be used alone in the methods described herein, or can be included as part of a fusion protein.

In some embodiments, the soluble ST2 polypeptide can be of sufficient length to bind a naturally-occurring ligand, e.g., IL33. Whether a soluble ST2 polypeptide can bind a naturally-occurring ligand can be determined, e.g., using a binding assay described herein. The soluble ST2 polypeptide can include, e.g., at least about 30, e.g., at least about 50, 75, 100, 150, 200, 250, or 300, of amino acids 1-336 of SEQ ID NO:2. In one embodiment, the soluble ST2 polypeptide includes amino acids 1-336 of SEQ ID NO:2 with no more than one, e.g., 2, 3, 4, 8, 10, 12, 15, 20, 30, 40 or 50, conservative amino acid substitutions. In one embodiment, the amino acid sequence of the soluble ST2 polypeptide differs, e.g., by substitution, deletion or insertion, by no more than one, e.g., 2, 3, 4, 8, 10, 12, 15, 20, 30, 40 or 50, from amino acids 1-336 of SEQ ID NO:2.

In one embodiment, the ST2-modulating agent is a soluble ST2 polypeptide (e.g., a soluble ST2 polypeptide described herein) fused to a heterologous polypeptide to form an ST2 fusion protein. The heterologous polypeptide can be, e.g., all or a portion of an immunoglobulin (e.g., a mouse or human immunoglobulin), e.g., all or a portion of an Fc region (e.g., a mouse or human Fc region). For example, the heterologous polypeptide can include all or a portion of the CH2 domain, the CH3 domain, and/or a hinge region, of an immunoglobulin, e.g., a mouse or human immunoglobulin. An exemplary heterologous polypeptide includes amino acid residues 339-571 of SEQ ID NO:2. The heterologous polypeptide can include, e.g., about 100, 150, or 200, of amino acids 339-571 of SEQ ID NO:2.

Preferably, the heterologous polypeptide is an Fc region from a human immunoglobulin.

In one embodiment, the heterologous polypeptide is an Fc region that has been altered to have increased or decreased antibody dependent cellular cytotoxicity (ADCC), complement-mediated cytotoxicity or Fc receptor binding. For example, the Asparagine residue at position 297 of the Fc region can be mutated to an amino acid residue other than Asparagine.

In one embodiment, the ST2-modulating agent is a fusion protein that includes a soluble ST2 polypeptide described herein joined to a heterologous polypeptide described herein by a linker. The linker can be a peptide having, e.g., 2, 3, 4, 5, or 10 amino acids, that are not derived from the ends of the soluble ST2 polypeptide or the heterologous polypeptide that are joined. One such exemplary fusion protein is an ST2-Fc fusion protein that includes amino acids 1-571 of SEQ ID NO:2.

In one embodiment, the ST2-modulating agent is an anti-ST2 antibody, or antigen-binding fragment, described herein. In one embodiment, the ST2-modulating agent is a small molecule described herein. In one embodiment, the ST2-modulating agent is a soluble, nonactivating fragment of a naturally-occurring ligand (e.g., IL33), or a nonactive mutant of a naturally-occurring ligand (e.g., IL33).

The types of lung fibrosis that can be treated or prevented using the methods described herein include, e.g., lung or pulmonary fibrosis associated with idiopathic pulmonary fibrosis, adult respiratory distress syndrome, fibrosis with collagen vascular disease, bronchiolitis obliterans, respiratory bronchiolitis, sarcoidosis, histiocytosis X, Hermansky-Pudlak syndrome, nonspecific interstitial pneumonia, acute interstitial pneumonia, lymphocytic interstitial pneumonia, and cryptogenic organizing pneumonia. Typically, the lung fibrosis is idiopathic pulmonary fibrosis.

The subject can be a mammal, e.g., a primate, preferably a higher primate, e.g., a human (e.g., a patient having, or at risk of, lung fibrosis). In one embodiment, the subject is a patient having lung fibrosis. The subject can be, e.g., a human subject between the ages of 6 and 18 years, 18 and 35 years, 35 and 65 years, or more than 65 years old. The subject can be male or female and can have various stages or levels of affliction. The subject can also be an experimental animal, e.g., an animal model for lung fibrosis.

In one embodiment, the subject is at risk of lung fibrosis, e.g., is undergoing radiation therapy or chemotherapy; has a family history of or genetic factors indicating a predisposition to lung fibrosis; has an occupation involving exposure to radiation, toxic agents, or inhalation of dusts or noxious vapors; or is suffering from an infection that may lead to complications that include lung fibrosis.

An ST2-modulating agent described herein, e.g., a soluble ST2 polypeptide, e.g., an ST2 fusion protein, can be administered to the subject systemically (e.g., intravenously, intramuscularly, by infusion, e.g., using an infusion device, subcutaneously, transdermally, or by inhalation). In embodiments where the ST2-modulating agent is a small molecule, it can be administered orally.

Preferably, the ST2-modulating agent is administered at a dose between about 0.001 and about 50 mg inhibitor per kg body weight, more preferably, between about 0.01 and about 10 mg inhibitor per kg body weight, most preferably between about 0.1 and about 4 mg inhibitor per kg body weight.

In one embodiment, the ST2-modulating agent is administered in an amount sufficient to reduce lung fibrosis, e.g., by at least 5, 10, 15, 20, 40, 50, 60, 70, or 80% or more, in lung tissue, relative to the fibrosis in an untreated subject. The amount sufficient to reduce fibrosis can be evaluated using an animal model, e.g., as described herein.

In one embodiment, the ST2-modulating agent is administered in an amount sufficient to improve symptoms in one or more lung fibrosis assessment criterion, e.g., a criterion or scale described herein, by at least 5, 10, 15, 20, 40, 50, 60, 70, or 80% or more, or by a half-step or full step in the scale.

In one embodiment, the subject is evaluated for lung fibrosis after treatment with the ST2-modulating agent, e.g., a soluble ST2 polypeptide, e.g., an ST2 fusion protein. In some embodiments, the evaluation is performed at least 1 hour, e.g., at least 2, 4, 6, 8, 12, 24, or 48 hours, or at least 1 week, 2 weeks, 4 weeks, 10 weeks, 13 weeks, 20 weeks or more, after the administration of the ST2-modulating agent. The subject can be evaluated in one or more of the following periods: prior to beginning of treatment; during the treatment; or after one or more elements of the treatment have been administered. Evaluating can include evaluating the need for further treatment with the same ST2-modulating agent or for additional treatment with additional agents. In a preferred embodiment, if a preselected outcome of the evaluation is obtained, an additional step is taken, e.g., the subject is administered another treatment or another evaluation or test is performed.

In one embodiment, the method includes treating a subject that has been treated previously with a therapeutic agent for lung fibrosis, e.g., has been treated previously with a corticosteroid (e.g., prednisone) or cytoxan. In another embodiment, the method includes treating a subject that has not been previously treated previously with a therapeutic agent for lung fibrosis.

In one embodiment, the method can further include the step of analyzing a nucleic acid or protein from the subject, e.g., analyzing the genotype of the subject. In one embodiment, a nucleic acid encoding human ST2 and/or an upstream or downstream component(s) of human ST2 signaling, e.g., an extracellular or intracellular activator or inhibitor of human ST2, is analyzed. The analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment, but preferably, prior to administration of the ST2-modulating agent to thereby determine appropriate dosage(s) and treatment regimen(s) of the ST2-modulating agent (e.g., amount per treatment or frequency of treatments) for prophylactic or therapeutic treatment of the subject.

In another embodiment, the method further includes the administration of an ST2-modulating agent described herein in combination with other therapeutic modalities. For example, the ST2-modulating agent can be administered in combination with a therapeutically effective amount of a second agent selected from the group consisting of corticosteroids (e.g., prednisone), cytotoxic drugs (e.g., cyclophosphamide or azathioprine), penicillamine, colchicines, interferon γ, 2-oxoglutarate analogs, prostaglandin analogs, Adefovir and Irbesartan. The ST2-modulating agent and the second agent can be administered sequentially or at the same time, e.g., where the course of administration of the ST2-modulating agent overlaps with the course of the second agent, or where there is at least a point in time at which there are therapeutic levels of both agents in the subject. Any suitable combination and sequence of systemic agents can be used. The ST2-modulating agent and the second agent can be administered during periods of active disease (e.g., when the subject is actively suffering from lung fibrosis), and/or during a period of remission or less active disease (e.g., when lung fibrosis in remission or reduced in severity). The ST2-modulating agent and the second agent can be administered before treatment, concurrently with treatment, post treatment, or during remission of the lung fibrosis.

In preferred embodiments, the amount of a second agent therapeutically effective to treat a subject having lung fibrosis is reduced compared to the amount of the second agent therapeutically effective to treat the subject in the absence of the ST2-modulating agent. The reduction and/or elimination of the second agent can be over an extended period of time, e.g., 15 days, 1 month, 2 months, 3 months, 6 months, 1, 2, 3, 4 years or more. In another embodiment, the amount of the second agent administered to treat the fibrosis is reduced by at least 5%, 10%, 20%, 30%, 50% or more as compared to the amount administered in the absence of administration of the ST2-modulating agent. The reduction of the second agent can refer to the time frame of the administration(s) or the amount of the administration or both.

In another aspect, the invention provides methods of treating lung fibrosis in a subject. The method includes administering to the subject a soluble ST2 polypeptide fused to an Fc region of an immunoglobulin in an amount effective to treat lung fibrosis. In some embodiments, the soluble ST2 polypeptide lacks a sufficient portion of its membrane-spanning domain to anchor the polypeptide or is modified such that the membrane-spanning domain is non-functional. In some embodiments, the soluble ST2 polypeptide includes the entire extracellular sequence. An exemplary soluble ST2 polypeptide includes amino acids 1-336 depicted in FIG. 12A (SEQ ID NO:2).

In some embodiments, the soluble ST2 polypeptide can be of sufficient length to bind a naturally-occurring ligand, e.g., IL33. Whether a soluble ST2 polypeptide can bind a naturally-occurring ligand can be determined, e.g., using a binding assay described herein. The soluble ST2 polypeptide can include, e.g., about 30, e.g., about 50, 75, 100, 150, 200, 250, or 300, of amino acids 1-336 of SEQ ID NO:2. In one embodiment, the soluble ST2 polypeptide includes amino acids 1-336 of SEQ ID NO:2 with no more than one, e.g., 2, 3, 4, 8, 10, 12, 15, 20, 30, 40 or 50, conservative amino acid substitutions. In one embodiment, the amino acid sequence of the soluble ST2 polypeptide differs, e.g., by substitution, deletion or insertion, by no more than one, e.g., 2, 3, 4, 8, 10, 12, 15, 20, 30, 40 or 50, from amino acids 1-336 of SEQ ID NO:2.

In one embodiment, the Fc region includes all or a portion of the CH2 domain, all or a portion of the CH3 domain, and/or all or a portion of a hinge region, of an immunoglobulin, e.g., a mouse or human immunoglobulin. An exemplary Fc region includes amino acid residues 339-571 of SEQ ID NO:2. The Fc region can include, e.g., about 100, 150, or 200, of amino acids 339-571 of SEQ ID NO:2.

In a preferable embodiment, the Fc region is from a human immunoglobulin.

In one embodiment, the Fc region has been altered to have increased or decreased antibody dependent cellular cytotoxicity (ADCC), complement-mediated cytotoxicity or Fc receptor binding. For example, the Asparagine residue at position 297 of the Fc region can be mutated to an amino acid residue other than Asparagine.

In one embodiment, the soluble ST2 polypeptide is joined to an Fc region of an immunoglobulin by a linker. The linker can be a peptide having, e.g., 2, 3, 4, 5, or 10 amino acids, that are not derived from the ends of the soluble ST2 polypeptide or the Fc region that are joined.

In another aspect, the invention provides methods to treat liver fibrosis in a subject. The method includes administering to the subject an ST2-modulating agent, e.g., an ST2 inhibitor, e.g., an sST2 inhibitor, e.g., an agent that decreases the activity, level or expression of sST2 or a naturally-occurring ligand of sST2, in an amount effective to treat liver fibrosis.

In a preferred embodiment, the agent is an inhibitor that decreases the expression, translation, or activity of sST2. In one embodiment, the agent can directly inhibit the activity, expression or processing of sST2. For example, the agent can interact with, e.g., bind to, a sST2 protein and block or reduce sST2 activity. In other embodiments, the agent can block or reduce expression of sST2, e.g., by reducing transcription or translation of sST2 mRNA, or reducing the stability of sST2 mRNA or protein. In still other embodiments, the agent can block the processing of sST2, e.g., the agent can inhibit one or more of: the conversion of sST2 from a precursor to active form, or the release or secretion of active or latent forms of sST2. Alternatively, the agent can indirectly inhibit sST2 by inhibiting the activity or expression of: an upstream sST2 activator, an enzyme involved in the conversion of sST2 from latent to active form, or a downstream sST2 activator target, or can increase the activity or expression of an sST2 inhibitor, or a downstream sST2 inhibitor target.

In one embodiment, the ST2-modulating agent, e.g., ST2 inhibitor, is an anti-ST2 antibody, e.g., an anti-sST2 antibody, or antigen-binding fragment thereof. The anti-ST2 antibody, e.g., anti-sST2 antibody, can be, e.g., a monospecific antibody (e.g., a monoclonal antibody) or an antigen-binding fragment thereof. The anti-ST2 antibody (e.g., recombinant or modified antibody) can be full-length (e.g., an IgG (e.g., an IgG1, IgG2, IgG3, IgG4), IgM, IgA (e.g., IgA1, IgA2), IgD, and IgE, but preferably an IgG) or can include only an antigen-binding fragment (e.g., a Fab, F(ab')$_2$ or scFv fragment, or one or more CDRs). An antibody, or antigen-binding fragment thereof, can include two heavy chain immunoglobulins and two light chain immunoglobulins, or can be a single chain antibody. The antibody can, optionally, include a constant region chosen from a kappa, lambda, alpha, gamma, delta, epsilon or a mu constant region gene. In some embodiments, the anti-ST2 antibody includes a heavy and light chain constant region substantially from a human antibody, e.g., a human IgG1 constant region or a portion thereof. In some embodiments, the anti-ST2 antibody is a human antibody.

In other embodiments, the antibody (or antigen-binding fragment thereof) is a recombinant or modified anti-ST2 antibody chosen from, e.g., a chimeric, a humanized, a deimmunized, or an in vitro generated antibody. As discussed herein, the modified antibodies can be CDR-grafted, humanized, deimmunized, or more generally, antibodies having CDRs from a non-human antibody and a framework that is selected as less immunogenic in humans, e.g., less antigenic than the murine framework in which a murine CDR naturally occurs.

In one embodiment, the ST2-modulating agent is an inhibitor of the expression or translation of an ST2 nucleic acid, such as a double-stranded RNA (dsRNA) molecule, an antisense molecule, a ribozyme, a triple helix molecule, or any combination thereof.

In one embodiment, the ST2-modulating agent, e.g., ST2 inhibitor, is a small molecule described herein (e.g., a chemical agent having a molecular weight of less than 2500 Da, preferably, less than 1500 Da), or a chemical, e.g., a small organic molecule.

The types of liver fibrosis that can be treated or prevented include, e.g., liver or hepatic fibrosis caused by, e.g., pathogens (e.g., hepatitis B, C, or D virus, or liver fluke), autoimmune conditions, exposure to a drug or chemical (e.g., Rezulin®, Serzone®, paracetamol, or pyrrolizidine alkaloids), consumption of alcohol, inherited conditions (e.g., hepatic hemochromatosis, Wilson's disease or alpha-1-antitrypsin deficiency), primary biliary cirrhosis, autoimmune chronic active hepatitis, and schistosomiasis.

The subject can be a mammal, e.g., a primate, preferably a higher primate, e.g., a human (e.g., a patient having, or at risk of, liver fibrosis). In one embodiment, the subject is a patient having liver fibrosis. The subject can be, e.g., a human subject between the ages of 6 and 18 years, 18 and 35 years, 35 and 65 years, or more than 65 years old. The subject can be male or female and can have various stages or levels of affliction. The subject can also be an experimental animal, e.g., an animal model for liver fibrosis.

An ST2-modulating agent described herein, e.g., an ST2 inhibitor, can be administered to the subject systemically (e.g., intravenously, intramuscularly, by infusion, e.g., using an infusion device, subcutaneously, transdermally, or by inhalation). In embodiments where the ST2-modulating agent is a small molecule, it can be administered orally.

Preferably, the ST2-modulating agent is administered at a dose between about 0.001 and about 50 mg inhibitor per kg body weight, more preferably, between about 0.01 and about 10 mg inhibitor per kg body weight, most preferably between about 0.1 and about 4 mg inhibitor per kg body weight.

In one embodiment, the ST2-modulating agent is administered in an amount sufficient to reduce liver fibrosis, e.g., by at least 5, 10, 15, 20, 40, 50, 60, 70, or 80% or more, in liver tissue, relative to the fibrosis in an untreated subject. The amount sufficient to reduce fibrosis can be evaluated using an animal model, e.g., as described herein.

In one embodiment, the ST2-modulating agent is administered in an amount sufficient to improve symptoms in one or more liver fibrosis assessment criterion, e.g., a criterion or scale described herein, by at least 5, 10, 15, 20, 40, 50, 60, 70, or 80% or more, or by a half-step or full step in the scale.

In one embodiment, the subject is evaluated for liver fibrosis after treatment with the ST2-modulating agent, e.g., an ST2 inhibitor. In some embodiments, the evaluation is performed at least 1 hour, e.g., at least 2, 4, 6, 8, 12, 24, or 48 hours, or at least 1 week, 2 weeks, 4 weeks, 10 weeks, 13 weeks, 20 weeks or more, after the administration of the ST2-modulating agent. The subject can be evaluated for liver fibrosis using a method described herein. The subject can be evaluated in one or more of the following periods: prior to beginning of treatment; during the treatment; or after one or more elements of the treatment have been administered. Evaluating can include evaluating the need for further treatment with the same ST2-modulating agent or for additional treatment with additional agents. In a preferred embodiment, if a preselected outcome of the evaluation is obtained, an additional step is taken, e.g., the subject is administered another treatment or another evaluation or test is performed.

In one embodiment, the method includes treating a subject that has been treated previously with a therapeutic agent for liver fibrosis. In another embodiment, the method includes treating a subject that has not been previously treated previously with a therapeutic agent for liver fibrosis.

In one embodiment, the method can further include the step of analyzing a nucleic acid or protein from the subject, e.g., analyzing the genotype of the subject. In one embodiment, a nucleic acid encoding human ST2 and/or an upstream or downstream component(s) of human ST2 signaling, e.g., an extracellular or intracellular activator or inhibitor of human ST2, is analyzed. The analysis can be used, e.g., to evaluate the suitability of, or to choose between alternative treatments, e.g., a particular dosage, mode of delivery, time of delivery, inclusion of adjunctive therapy, e.g., administration in combination with a second agent, or generally to determine the subject's probable drug response phenotype or genotype. The nucleic acid or protein can be analyzed at any stage of treatment, but preferably, prior to administration of the ST2-modulating agent to thereby determine appropriate dosage(s) and treatment regimen(s) of the ST2-modulating agent (e.g., amount per treatment or frequency of treatments) for prophylactic or therapeutic treatment of the subject.

In another embodiment, the method further includes the administration of an ST2-modulating agent described herein in combination with other therapeutic modalities. For example, the ST2-modulating agent can be administered in combination with a therapeutically effective amount of a second agent selected from the group consisting of corticosteroids (e.g., prednisone), cytotoxic drugs (e.g., cyclophosphamide or azathioprine), penicillamine, colchicines, interferon γ, 2-oxoglutarate analogs, prostaglandin analogs, Adefovir and Irbesartan. The ST2-modulating agent and the second agent can be administered sequentially or at the same time, e.g., where the course of administration of the ST2-modulating agent overlaps with the course of the second agent, e.g., where there is at least a point in time at which there are therapeutic levels of both agents in the subject. Any suitable combination and sequence of systemic agents can be used. The ST2-modulating agent and the second agent can be administered during periods of active disease (e.g., when the subject is actively suffering from liver fibrosis), and/or during a period of remission or less active disease (e.g., when liver fibrosis in remission or reduced in severity). The ST2-modulating agent and the second agent can be administered before treatment, concurrently with treatment, post treatment, or during remission of the liver fibrosis.

In preferred embodiments, the amount of a second agent therapeutically effective to treat a subject having liver fibrosis is reduced compared to the amount of the second agent therapeutically effective to treat the subject in the absence of the ST2-modulating agent. The reduction and/or elimination of the second agent can be over an extended period of time, e.g., 15 days, 1 month, 2 months, 3 months, 6 months, 1, 2, 3, 4 years or more. In another embodiment, the amount of the second agent administered to treat the fibrosis is reduced by at least 5%, 10%, 20%, 30%, 50% or more as compared to the amount administered in the absence of administration of the ST2-modulating agent. The reduction of the second agent can refer to the time frame of the administration(s) or the amount of the administration or both.

In another aspect, the invention provides compositions that include an ST2-modulating agent described herein. The composition can include, e.g., an ST2 polypeptide, e.g., a soluble ST2 polypeptide, e.g., an ST2 fusion protein described herein, and/or an anti-ST2 antibody, e.g., anti-sST2 antibody described herein. Preferably, the composition includes an ST2-Fc fusion protein, e.g., an ST2-Fc fusion protein having an ST2 polypeptide depicted by amino acids 1-336 of SEQ ID NO:2, and a human Fc region. The compositions described can further include a pharmaceutically acceptable carrier, excipient or stabilizer.

In another aspect, the invention features a kit, which includes an ST2-modulating agent described herein. In one embodiment, the kit includes (a) a container that contains a composition that includes both an ST2-modulating agent, e.g., an ST2-Fc fusion protein, e.g., an ST2-Fc fusion protein having an ST2 polypeptide depicted by amino acids 1-336 of SEQ ID NO:2 and a human Fc region and, optionally (b) informational material. In one embodiment, the kit includes (a) a container that contains a composition that includes both an ST2-modulating agent, e.g., an anti-ST2 antibody, e.g., an anti-sST2 antibody and, optionally (b) informational material. The informational material can be descriptive, instructional, marketing or other material that relates to the methods described herein and/or the use of the agents for therapeutic benefit.

The informational material of the kits is not limited in its form. In one embodiment, the informational material can include information about production of the ST2-modulating agent, molecular weight of the agent, concentration, date of expiration, batch or production site information, and so forth. In one embodiment, the informational material relates to methods of administering the ST2-modulating agent, e.g., in a suitable amount, manner, or mode of administration (e.g., a dose, dosage form, or mode of administration described herein). The method can be a method of treating fibrosis, e.g., lung or liver fibrosis.

The informational material, e.g., instructions, can be provided in printed matter, e.g., a printed text, drawing, and/or photograph, e.g., a label or printed sheet. The informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about agents therein and/or its use in the methods described herein. Of course, the informational material can also be provided in any combination of formats.

In addition to the ST2-modulating agent, the composition of the kit can include other ingredients, such as a solvent or buffer, a stabilizer, or a preservative. The kit may also include other agents, e.g., a second or third agent, e.g., other therapeutic agents.

The agents can be provided in any form, e.g., liquid, dried or lyophilized form. It is preferred that the agents are substantially pure (although they can be combined together or delivered separate from one another) and/or sterile. When the agents are provided in a liquid solution, the liquid solution preferably is an aqueous solution, with a sterile aqueous solution being preferred. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit can be contained within a single, undivided container. For example, the composition can be contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a unit dosage, e.g., a unit that includes the ST2-modulating agent. For example, the kit can include a plurality of syringes, ampules, foil packets, blister packs, or medical devices, e.g., each containing a unit dose. The containers of the kits can be air tight, waterproof (e.g., impermeable to changes in moisture or evaporation), and/or light-tight.

The kit can optionally include a device suitable for administration of the composition, e.g., a syringe or other suitable delivery device. The device can be provided pre-loaded with an ST2-modulating agent, e.g., in a unit dose, or can be empty, but suitable for loading.

An "ST2 modulator" or "ST2-modulating agent" refers to any compound that at least partially modulates the expression level or activity of ST2 e.g., a binding activity of ST2 or an ST2 signaling activity, e.g., ability to transduce a ST2-mediated signal. In the context of lung fibrosis, "ST2-modulating agent" refers to an agent that modulates, e.g., inhibits, the activity of ST2L, e.g., modulates (e.g., inhibits) the binding of ST2L to a cognate ligand of ST2L (e.g., IL33, see Schmitz et al., Immunity 23: 479-490, 2005). In this context, an ST2-modulating agent can bind to ST2L or to a ligand of ST2L, e.g., IL33. A typical ST2-modulating agent can bind to ST2L or to a ligand of ST2L, e.g., IL33, with a $K_d$ of less than $10^{-6}$, $10^{-7}$, $10^{-8}$, $10^{-9}$, or $10^{-10}$ M. In the context of liver fibrosis, "ST2-modulating agent" refers to an agent that modulates, e.g., inhibits, the activity of sST2, e.g., modulates (e.g., inhibits) the binding of sST2 to a cognate ligand of sST2. In the liver fibrosis context, an ST2-modulating agent can bind to sST2 or to a ligand of sST2. A typical ST2-modulating agent can bind to sST2 or to a ligand of sST2 with a $K_d$ of less than $10^{-6}$, $10^{-7}$, $10^{-8}$, $10^{-9}$, or $10^{-10}$ M.

As used herein, a "soluble ST2 polypeptide" is an ST2 polypeptide incapable of anchoring itself in a membrane. Such soluble polypeptides include, for example, ST2 polypeptides that lack a sufficient portion of their membrane-spanning domain to anchor the polypeptides or are modified such that the membrane-spanning domain is non-functional.

As used herein, the term "treatment", "treat" or "treating" refers to administering a therapy in an amount, manner, and/or mode effective to improve a condition, symptom, or parameter associated with a disorder (e.g., liver or lung fibrosis) or to reduce onset, progression, or exacerbation of the disorder, to either a statistically significant degree or to a degree detectable to one skilled in the art. Accordingly, treating can achieve therapeutic and/or prophylactic benefits. An effective amount, manner, or mode can vary depending on the subject and may be tailored to the subject. As used herein, "treatment" also encompasses the prophylactic treatment of subjects with an elevated risk for liver or lung fibrosis.

As used herein, "an amount effective to treat", or a "therapeutically effective amount", refers to an amount of an ST2-modulating agent that is effective, upon single or multiple dose administrations to a subject, to improve or prophylactically treat a condition, symptom, or parameter associated with a disorder or to reduce onset, progression, or exacerbation of the disorder, to either a statistically significant degree or to a degree detectable to one skilled in the art. For example, "an amount effective to treat" is an amount sufficient to reduce lung or liver fibrosis by at least 5, 10, 15, 20, 40, 50, 60, 70, or 80% or more, in fibrotic tissue, relative to the fibrosis in an untreated subject. Alternatively, "an amount effective to treat" is an amount sufficient to improve symptoms in one or more lung or liver assessment criterion described herein by at least 5, 10, 15, 20, 40, 50, 60, 70, or 80% or more.

The terms "induce," "inhibit," "potentiate," "elevate," "increase," "decrease," or the like, e.g., which denote quantitative differences between two states, refer to a difference, e.g., a statistically significant difference, between the two states.

In another example, "an amount of a second agent to treat fibrosis" means that the dosage of the second agent will be different, e.g., statistically different, than the dosage in the absence of administration of an ST2-modulating agent.

As used herein, "specific binding" refers to the property of the ST2-modulating agent to: (1) to bind to ST2, e.g., human ST2 protein, with an affinity of at least $1 \times 10^7$ $M^{-1}$, and (2) preferentially bind to ST2, e.g., human ST2 protein, with an affinity that is at least two-fold, 50-fold, 100-fold, 1000-fold, or more greater than its affinity for binding to a non-specific antigen (e.g., BSA, casein) other than ST2.

As used herein, the term "antibody" refers to a protein comprising at least one, and preferably two, heavy (H) chain variable regions (abbreviated herein as VH), and at least one and preferably two light (L) chain variable regions (abbreviated herein as VL). The VH and VL regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196:901-917, which are incorporated herein by reference). Preferably, each VH and VL is composed of three CDRs and four FRs, arranged from amino-terminus to carboxyl-terminus in the following order: FR1, CDR1, FR2, CDR2, FR3, CDR3, FR4.

The VH or VL chain of the antibody can further include all or part of a heavy or light chain constant region. In one embodiment, the antibody is a tetramer of two heavy immunoglobulin chains and two light immunoglobulin chains, wherein the heavy and light immunoglobulin chains are interconnected by, e.g., disulfide bonds. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the amino terminus (about 110 amino acids) and a kappa or lambda constant region gene at the carboxyl terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids). The term "immunoglobulin" includes an immunoglobulin having: CDRs from a non-human source, e.g., from a non-human antibody, e.g., from a mouse immunoglobulin or another non-human immunoglobulin, from a consensus sequence, or from a sequence generated by phage display, or any other method of generating diversity; and having a framework that is less antigenic in a human than a non-human framework, e.g., in the case of CDRs from a non-human immunoglobulin, less antigenic than the non-human framework from which the non-human CDRs were taken. The framework of the immunoglobulin can be human, humanized non-human, e.g., a mouse, framework modified to decrease antigenicity in humans, or a synthetic framework, e.g., a consensus sequence. These are sometimes referred to herein as modified immunoglobulins. A modified antibody, or antigen binding fragment thereof, includes at least one, two, three or four modified immunoglobulin chains, e.g., at least one or two modified immunoglobulin light and/or at least one or two modified heavy chains. In one embodiment, the modified antibody is a tetramer of two modified heavy immunoglobulin chains and two modified light immunoglobulin chains.

The term "antigen-binding fragment" of an antibody (or simply "antibody portion," or "fragment"), as used herein, refers to a portion of an antibody which specifically binds to ST2 (e.g., human ST2), e.g., a molecule in which one or more immunoglobulin chains is not full length but which specifically binds to ST2 (e.g., human ST2 protein). Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al, (1989) *Nature* 341:544-546), which consists of a VH domain; and (vi) an isolated complementarity determining region (CDR) having sufficient framework to specifically bind, e.g., an antigen binding portion of a variable region. An antigen binding portion of a light chain variable region and an antigen binding portion of a heavy chain variable region, e.g., the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

As used herein, the term "substantially identical" (or "substantially homologous") is used herein to refer to a first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same specificity and has at least 50% of the affinity of the same.

Calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent homology between two sequences can be accomplished using a mathematical algorithm. In a preferred embodiment, the percent homology between two amino acid sequences is determined using the Needleman and Wunsch (1970), *J. Mol. Biol.* 48:444-453, algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent homology between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a homology limitation of the invention) are a Blossum 62 scoring matrix with a gap penalty of 12, a gap extend penalty of 4, and a frameshift gap penalty of 5.

It is understood that the ST2-modulating agents, e.g., soluble ST2 polypeptides described herein, may have additional conservative or non-essential amino acid substitutions, which do not have a substantial effect on the polypeptide functions. Whether or not a particular substitution will be tolerated, i.e., will not adversely affect desired biological properties, such as binding activity can be determined as described in Bowie, J U et al. (1990) *Science* 247:1306-1310. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

A "non-essential" amino acid residue is a residue that can be altered from the wild-type sequence of the ST2-modulating agent, e.g., a soluble ST2 polypeptide, without abolishing or more preferably, without substantially altering a biological activity, whereas an "essential" amino acid residue results in such a change.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control.

BRIEF DESCRIPTION OF DRAWINGS

FIG. 12A depicts the amino acid sequence (SEQ ID NO:2) of ST2-Fc. Amino acids 1-336 depict the ST2 polypeptide, amino acids 337-338 depict a linker sequence, and amino acids 339-571 depict the Fc region. FIG. 12B depicts the nucleic acid sequence (SEQ ID NO:1) of ST2-Fc.

DETAILED DESCRIPTION

Figure 1:
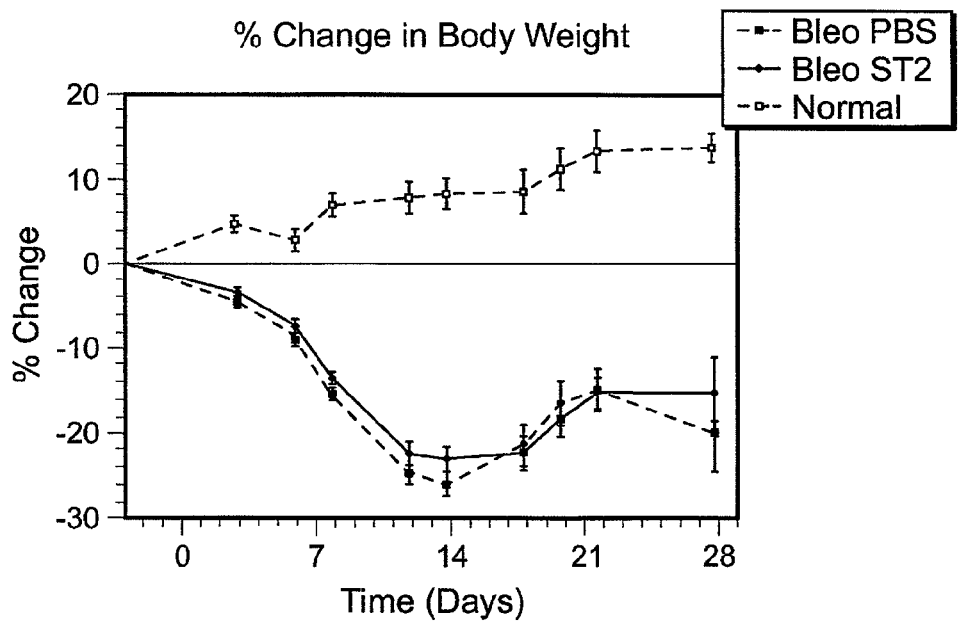
FIG. 1 is a graph of percent change in body weight of mice treated with bleomycin and PBS, bleomycin and ST2-Fc.

The methods described herein relate generally to the treatment of subjects having fibrosis, e.g., lung or liver fibrosis, with an ST2-modulating agent, e.g., a soluble ST2 polypeptide, e.g., an ST2 fusion protein, e.g., ST2-Fc.

ST2

The IL-1R related gene ST2 encodes a secreted (sST2) and a membrane bound (ST2L) protein (Bergers et al., (1994), *EMBO J.* 13: 1176-1188). ST2 is known to be expressed in various species (Tominaga et al., (1991), *Biochim. Biophys. Acta.* 1090: 1-8; Tominaga et al., (1992), *Biochim. Biophys. Acta* 1171:215-218; Iwahana et al, (2004) *Biochim. Biophys. Acta* 1681: 1-14). The production of sST2 was originally discovered in fibroblasts and subsequently found to be secreted by human and mouse macrophages and by human Th2 cells (Bergers et al., (1994), *EMBO J.* 13: 1176-1188; Saccani et al., (1998), *Cytokine* 10: 773-779; Oshikawa et al., (2002), *Biochem. Biophys. Res. Commun.* 299: 18-24; Lecart et al., (2002), *Eur. J. Immunol.* 32: 2979-2987). ST2L also appears to be a stable and selective marker expressed by mouse and human Th2 cells (characterized by a discrete cytokine pattern including IL-4, -5, -9, -10, -13, -25, and -31), but not by Th1 cells (Lecart et al., (2002), *Eur. J. Immunol.* 32: 2979-2987; Lohning et al., (1998), *PNAS USA.* 95: 6930-6935; Xu et al, (1998), *J. Exp. Med.* 187: 787-7). ST2L is also expressed by mouse IL-10 secreting type 1 regulatory T cells (Tr1), IL-4 producing mastocytes, and human Tc2 and NK2 cell lines (McGuirk et al., (2002), *J. Exp. Med.* 195: 221-231; Lecart et al., (2001), *J. Invest. Dermatol.* 117: 318-325; Gachter et al., (1996), *J. Biol. Chem.* 271: 124-129; Chan et al., (2001), *J. Immunol.* 167: 1238-44). In vitro, ST2L expression by Th2 cells is significantly up-regulated by pro-inflammatory cytokines IL-6, IL-1 and TNFα, and suppressed by a Th1 cytokine IFNγ (Meisel et al., (2001), *J. Immunol.* 166: 3143-3150; Carter et al., (2001), *Eur. J. Immunol.* 31: 2979-2985). Recently, a ligand for ST2L has been identified as IL33 (Schmitz et al., *Immunity* 23: 479-490, 2005).

Cross-linking of ST2L on Th2 cells stimulates production of type 2 cytokines (Meisel et al., (2001), *J. Immunol.* 166: 3143-3150). In murine respiratory mucosa, ST2 is expressed by alveolar macrophages, activated CD4$^+$ T cells, and Tr1 (Oshikawa et al., (2002), *Biochem. Biophys. Res. Commun.* 299: 18-24; Lohning et al., (1998), *PNAS USA.* 95: 6930-6935; Lambrecht et al., (2000), *J. Clin. Invest.* 106: 551-559; McGuirk et al., (2002), *J. Exp. Med.* 195: 221-231). sST2 appears in blood after airway allergen challenge (Oshikawa et al., (2000), *Clin. Exp. Allergy* 32: 1520-1526). Acute allergen challenge of mice results in expansion of dendritic cells (DC) and production of IL-4, -5, and -13 (Gajewska et al., (2001), *Am. J. Respir. Cell. Mol Biol.* 25: 326-334). Chronic allergen exposure leads to accumulation of ST2L$^+$CD4$^+$ T cells in the lungs (Johnson et al., (2004), *Am. J. Respir. Crit. Care Med.* 169:378-385). Interaction between ST2L on pulmonary Th2 and an unknown ligand on DC appears to be essential for airway eosinophilia (Lambrecht et al., (2000), *J. Clin. Invest.* 106: 551-559), as anti-ST2 monoclonal antibodies or ST2-Fc block eosinophilic inflammation, IgE, and IL-4, -5, and -13 production in allergen-challenged lung (Lohning et al., (1998), *PNAS USA.* 95: 6930-6935; Lambrecht et al., (2000), *J. Clin. Invest.* 106: 551-559; Coyle et al., (1999), *J. Exp. Med.* 190:895-902).

Similarly, Th2 inflammation in respiratory mucosa and formation of primary pulmonary granuloma induced by *Schistosoma mansoni* are abrogated in ST2 knock out (KO) mice, and production of IL-4 and -5 is severely impaired (Townsend et al., (2000), *J. Exp. Med.* 191: 1069-1075). Also, anti-ST2 mAb injected during respiratory syncytial virus (RSV) infection selectively inhibits type 2, but not type 1 anti-RSV response in the lung (Walzl et al., (2001), *J. Exp. Med.* 193: 785-792). Positive regulation of pulmonary Th2 response by ST2L holds true both for "Th2-prone" BALB/c and for "Th1-prone" C57BL/6 mice (Lohning et al., (1998), *PNAS USA.* 95: 6930-6935; Lambrecht et al., (2000), *J. Clin. Invest.* 106: 551-559; Gajewska et al., (2001), *Am. J. Respir. Cell. Mol. Biol.* 25: 326-334; Coyle et al., (1999), *J. Exp. Med.* 190:895-902; Townsend et al., (2000), *J. Exp. Med.* 191: 1069-1075; Walzl et al., (2001), *J. Exp. Med.* 193: 785-792).

Secreted ST2 (sST2) also suppresses the expression of Toll-like receptors (TLR)-1, -2, -4 and -9 by macrophages. sST2 may signal through an unknown receptor that is up-regulated upon TLR-4 engagement (Sweet et al., (2001), *J. Immunol.* 166:6633-6639; Brint et al., (2004), *Nat. Immunol.* 5:373-379). As a result, pro-inflammatory cytokines IL-6, IL-12, IL-1, and TNFα are down-regulated, and mice are protected from endotoxic shock (Sweet et al., (2001), *J. Immunol.* 166:6633-6639; Brint et al., (2004), *Nat. Immunol.* 5:373-379). Moreover, the intracellular Toll-interleukin 1 receptor domain of ST2L inhibits signaling through IL-1R and TLR-4 by sequestering their adaptor proteins MyD88 and Mal (Brint et al., (2004), *Nat. Immunol.* 5 :373-379). Thus, both sST2 and ST2L negatively regulate TLR-supported Th1 response. In accordance with this model, ST2-Fc injected in vivo suppressed Th1 driven collagen-induced arthritis and down regulated IL-6, IL-12, IFNγ, and TNFα (Leung et al., (2004), *J. Immunol.* 173:145-150).

However, the role of ST2 pathway in regulation of Th1/Th2 balance is not always clear. For example, in intestinal tract of ST2 KO or sST2 transgenic (TG) mice, effector Th2 response to *Nippostrongylus brasiliensis* is intact (Senn et al., (2000), *Eur. J. Immunol.* 30:1929-1938). Similarly, treatment with ST2-Fc or with anti-ST2 mAb fails to abrogate Th2 response in footpads of *Leishmania major* infected BALB/c mice (Kropf et al., (2003), *Infection and Immunity* 71: 1961-1971).
Modulators of ST2

Any agent capable of modulating the level of expression or activity of ST2, ST2L or sST2 is useful in the methods described herein. Such modulators include, e.g., soluble ST2 polypeptides (e.g., ST2 fusion proteins), anti-ST2 antibodies, or antigen binding portions thereof, small molecules (e.g., a chemical agent having a molecular weight of less than 2500 Da, preferably, less than 1500 Da, a chemical, e.g., a small organic molecule, e.g., a product of a combinatorial library), ST2 mimetic agents and derivatives thereof. An agent that modulates the level of expression or activity of ST2, ST2L or sST2 can either increase or decrease the level of expression or activity. The expression can be modulated, e.g., increased or decreased, at the nucleic acid or protein level. The activity can be modulated, e.g., increased or decreased, by modulating, e.g., a signaling pathway in which ST2, ST2L or sST2 is involved.

Soluble ST2 Polypeptides

Soluble ST2 polypeptides that modulate ST2 are useful in the methods described herein. Soluble ST2 polypeptides include, e.g., the secreted form of ST2 (sST2, discussed in Bergers et al., (1994), *EMBO J.* 13: 1176-1188) or a fragment thereof. Soluble ST2 polypeptides also include ST2 polypeptides derived from a membrane-bound form of ST2 (ST2L), which include at least a portion of ST2 extracellular domain and are incapable of being anchored in a membrane. Such soluble polypeptides include, for example, ST2L-derived polypeptides that lack a sufficient portion of their membrane-spanning domain to anchor the polypeptide or are modified such that the membrane-spanning domain is non-functional.

ST2 Fusion Proteins

Soluble ST2 polypeptides also include soluble fusion proteins that include at least a portion of sST2, or the extracellular ST2 domain of ST2L, or a portion thereof, fused to a heterologous polypeptide. In one embodiment, the heterologous polypeptide is an immunoglobulin or a portion thereof. For example, the heterologous polypeptide can be an Fc region of an immunoglobulin, or a portion thereof. Preferred fusion proteins of this type contain the amino terminal 336 amino acids of murine ST2L (GenBank Accession Number D13695), as depicted in FIG. 12A (i.e., amino acids 1-336 of SEQ ID NO:2), and the Fc region of an immunoglobulin, e.g., an Fc region of a human immunoglobulin.

Production of Soluble ST2 Polypeptides

The soluble polypeptides useful in the methods described herein can be produced by a variety of methods known in the art. For example, the polypeptides can be derived from intact transmembrane ST2 polypeptides, e.g., ST2L polypeptides, by proteolysis using specific endopeptidases in combination with exopeptidases, Edman degradation, or both. The intact ST2 polypeptides, e.g., ST2L polypeptides, can be purified from its natural source using conventional methods. Alternatively, the intact ST2 polypeptide, e.g., ST2L polypeptide, can be produced by known recombinant DNA techniques using cDNAs.

Preferably, the soluble polypeptides useful in the methods of the present disclosure are produced directly, thus eliminating the need for an entire ST2 polypeptide as a starting material. This may be achieved by conventional chemical synthesis techniques or by well-known recombinant DNA techniques wherein only those DNA sequences that encode the desired peptides are expressed in transformed hosts. For example, a gene that encodes the desired soluble ST2 polypeptide can be synthesized by chemical means using an oligonucleotide synthesizer. Such oligonucleotides are designed based on the amino acid sequence of the desired soluble ST2 polypeptide. Specific DNA sequences coding for the desired peptide also can be derived from the full length DNA sequence by isolation of specific restriction endonuclease fragments or by PCR synthesis of the specified region.

Standard methods can be applied to synthesize a gene encoding a soluble ST2 polypeptide that is useful in the methods described herein. For example, the complete amino acid sequence can be used to construct a back-translated gene. A DNA oligomer containing a nucleotide sequence coding for a soluble ST2 polypeptide useful in the methods described herein can be synthesized in a single step. Alternatively, several smaller oligonucleotides coding for portions of the desired polypeptide can be synthesized and then ligated. Preferably, a soluble ST2 polypeptide useful in the methods described herein will be synthesized as several separate oligonucleotides, which are subsequently linked together. The individual oligonucleotides typically contain 5' or 3' overhangs for complementary assembly.

Once assembled, preferred genes will be characterized by sequences that are recognized by restriction endonucleases (including unique restriction sites for direct assembly into a cloning or an expression vector), preferred codons taking into consideration the host expression system to be used, and a sequence which, when transcribed, produces a stable, efficiently translated mRNA. Proper assembly may be confirmed by nucleotide sequencing, restriction mapping, and expression of a biologically active polypeptide in a suitable host.

It will be appreciated by those of skill in the art that, due to the degeneracy of the genetic code, DNA molecules comprising many other nucleotide sequences will also be capable of encoding the soluble ST2 polypeptides encoded by specific DNA sequences described herein. These degenerate sequences also code for polypeptides that are useful in the methods of this disclosure.

The DNA sequences may be expressed in unicellular hosts, or preferably in isolated mammalian host cells. As is well known in the art, to obtain high expression levels of a transfected gene in a host, the gene must be operatively linked to transcriptional and translational expression control sequences that are functional in the chosen expression host. Preferably, the expression control sequences, and the gene of interest, will be contained in an expression vector that further comprises a bacterial selection marker and origin of replication. If the expression host is a eukaryotic cell, the expression vector should further comprise an additional expression marker useful in the expression host.

The DNA sequences encoding the desired soluble polypeptides can encode a signal sequence. If the expression host is prokaryotic, it generally is preferred that the DNA sequence not encode a signal sequence. If the expression host is eukaryotic, it generally is preferred that a signal sequence be encoded.

An amino terminal methionine can be present on the expressed product. If the terminal methionine is not cleaved by the expression host, it can, if desired, be chemically removed by standard techniques.

A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from E. coli, including col E1, pCR1, pBR322, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof. Useful vectors for insect cells include pVL 941.

In addition, any of a wide variety of expression control sequences can be used in these vectors. Such useful expression control sequences include the expression control sequences associated with structural genes of the foregoing expression vectors. Examples of useful expression control sequences include, e.g., the early and late promoters of SV40 or adenovirus, the lac system, the trp system, the TAC or TRC system, the major operator and promoter regions of phage lambda, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes of prokaryotic or eukaryotic cells or their viruses, and various combinations thereof.

A wide variety of host cells are useful. Host cells can be a unicellular organism, or can be obtained from a multicellular organism, e.g., isolated cells from a multicellular host. These hosts can include well-known eukaryotic and prokaryotic hosts, such as strains of E. coli, Pseudomonas, Bacillus, Streptomyces, fungi, yeast, insect cells such as Spodoptera frugiperda (SF9), animal cells such as CHO and mouse cells, African green monkey cells such as COS 1, COS 7, BSC 1, BSC 40, and BMT 10, and human cells, as well as plant cells in tissue culture. For animal cell expression, CHO cells and COS 7 cells are preferred.

It should be understood that not all vectors and expression control sequences will function equally well to express the DNA sequences described herein. Neither will all hosts function equally well with the same expression system. One of skill in the art, however, may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the sequence, its controllability, and its compatibility with the DNA sequences discussed herein, particularly as regards potential secondary structures. Unicellular hosts should be selected by consideration of their compatibility with the chosen vector, the toxicity of the product coded for by the DNA sequences, their secretion characteristics, their ability to fold the soluble polypeptides correctly, their fermentation or culture requirements, and the ease of purification of the products coded for by the DNA sequences.

Within these parameters, one of skill in the art can select various vector/expression control sequence/host combinations that will express the desired DNA sequences on fermentation or in large scale animal culture, for example with CHO cells or COS 7 cells.

The soluble ST2 polypeptides can be isolated from the fermentation or cell culture and purified using any of a variety of conventional methods. One of skill in the art can select the most appropriate isolation and purification techniques.

While recombinant DNA techniques are the preferred method of producing useful soluble ST2 polypeptides having a sequence of more than 20 amino acids, shorter ST2 polypeptides having fewer than about 20 amino acids are preferably produced by conventional chemical synthesis techniques. Synthetically produced polypeptides useful in the methods of this disclosure can be advantageously produced in extremely high yields and can be easily purified.

Preferably, such soluble ST2 polypeptides are synthesized by solution phase or solid phase polypeptide synthesis and, optionally, digested with carboxypeptidase (to remove C-terminal amino acids) or degraded by manual Edman degradation (to remove N-terminal amino acids). The use of solution phase synthesis advantageously allows for the direct addition of certain derivatized amino acids to the growing polypeptide chain, such as the O-sulfate ester of tyrosine. This obviates the need for a subsequent derivatization step to modify any residue of the polypeptides useful in the methods of this disclosure.

Proper folding of the polypeptides may be achieved under oxidative conditions which favor disulfide bridge formation as described by Kent, "Chemical Synthesis of Polypeptides and Proteins," Ann. Rev. Biochem., 57, pp. 957-89 (1988). Polypeptides produced in this way may then be purified by separation techniques widely known in the art.

Soluble ST2 polypeptides can be assayed, e.g., for the ability to bind a naturally-occurring ligand, e.g., IL33, using known techniques. For example, the interaction between a soluble ST2 polypeptide and a ligand can be detected using a fluorescence assay in which at least one binding partner is fluorescently labeled. One example of such an assay includes fluorescence energy transfer (FET or FRET for fluorescence resonance energy transfer) (see, for example, Lakowicz et al., U.S. Pat. No. 5,631,169; Stavrianopoulos et al., U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, the "donor" protein molecule may simply utilize the natural fluorescent energy of tryptophan residues. Labels are chosen that emit different wavelengths of light, such that the "acceptor" molecule label may be differentiated from that of the "donor". Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP. See, e.g., Nasir et al. (1999) Comb Chem HTS 2:177-190; Jameson et al. (1995) Methods Enzymol 246:283; Seethala et al. (1998) Anal Biochem 255: 257. Fluorescence polarization can be monitored in multi-well plates. See, e.g., Parker et al. (2000) Journal of Biomolecular Screening 5:77-88; and Shoeman, et al. (1999) 38: 16802-16809.

In another embodiment, determining the ability of a soluble ST2 polypeptide to bind to naturally-occurring ligand can be accomplished using real-time Biomolecular Interaction Analysis (BIA) (see, e.g., Sjolander, S. and Urbaniczky, C. (1991) Anal. Chem. 63: 2338-2345; and Szabo et al. (1995) Curr. Opin. Struct. Biol. 5: 699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR), resulting in a detectable signal which can be used as an indication of real-time reactions between biological molecules. Other suitable assays that can be used are known in the art.

Anti-ST2 Antibodies

As used herein, an "antibody" is a protein comprising one or more polypeptides selected from immunoglobulin light chains and immunoglobulin heavy chains. The component polypeptides of an antibody composed of more than one polypeptide may optionally be disulfide-bound or otherwise covalently crosslinked. Accordingly, antibodies include intact immunoglobulins of types IgA, IgG, IgE, IgD, IgM (as well as subtypes thereof), wherein the light chains of the immunoglobulin may be of types kappa or lambda or antigen-binding portions thereof. The term includes recombinant antibodies, chimeric, CDR-grafted and humanized antibodies, or other antibodies modified to be less immunogenic in a human.

Also useful in the methods described herein are antigen-binding portions of antibodies, including portions of intact immunoglobulins that retain antigen-binding specificity, e.g., Fab fragments, Fab' fragments, F(ab')$_2$ fragments, F(v) fragments, heavy chain monomers or dimers, light chain monomers or dimers, dimers consisting of one heavy and one light chain, and the like.

As used herein, a "humanized recombinant antibody" or "humanized antibody" is an antibody, produced by recombinant DNA technology, in which some or all of the amino acids of a human immunoglobulin light or heavy chain that are required for antigen binding have been substituted for the corresponding amino acids from a nonhuman mammalian immunoglobulin light or heavy chain.

As used herein, a "chimeric recombinant antibody" is an antibody, produced by recombinant DNA technology, in which all or part of the hinge and constant regions of an immunoglobulin light chain, heavy chain, or both, have been substituted for the corresponding regions from another immunoglobulin light chain or heavy chain.

Many types of anti-ST2 antibodies are useful in the methods of this disclosure. These include monospecific (e.g., monoclonal) antibodies, recombinant antibodies, chimeric recombinant antibodies, humanized recombinant antibodies, as well as antigen-binding portions of the foregoing.

The technology for producing monoclonal antibodies is well known. See generally, Harlow, E. and Lane, D. (1988) *Antibodies: A Laboratory Manual*, Cold Spring Harbor Laboratory Press, Cold Spring Harbor, N.Y.; Kohler et al., *Nature*, "Continuous Cultures of Fused Cells Secreting Antibody of Predefined Specificity," 256, pp. 495-97 (1975). Useful immunogens for the purpose of the methods of this disclosure include ST2-bearing cells, as well as cell-free preparations containing ST2.

Immunization can be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. The lymphocytes used in the production of hybridoma cells typically are isolated from immunized mammals whose sera have already tested positive for the presence of the desired antibodies using such screening assays.

Anti-ST2 antibodies useful in the methods described herein can also be recombinant antibodies produced by host cells transformed with DNA encoding immunoglobulin light and heavy chains of a desired antibody. Recombinant antibodies may be produced by well-known genetic engineering techniques. See, e.g., U.S. Pat. No. 4,816,397, which is incorporated herein by reference. For example, recombinant antibodies may be produced by cloning cDNA or genomic DNA encoding the immunoglobulin light and heavy chains of the desired antibody from a hybridoma cell that produces an antibody useful in the methods of this disclosure. The cDNA or genomic DNA encoding those polypeptides is then inserted into expression vectors so that both genes are operatively linked to their own transcriptional and translational expression control sequences. The expression vector and expression control sequences are chosen to be compatible with the expression host cell used. Typically, both genes are inserted into the same expression vector.

Prokaryotic or eukaryotic host cells may be used. Expression in eukaryotic host cells is preferred because such cells are more likely than prokaryotic cells to assemble and secrete a properly folded and immunologically active antibody. It is possible that the host cells will produce portions of intact antibodies, such as light chain dimers or heavy chain dimers, which also are antibodies according to the methods described herein.

It will be understood that variations on the above procedure are useful in the methods described herein. For example, it may be desired to transform a host cell with DNA encoding either the light chain or the heavy chain (but not both) of an antibody homolog. Recombinant DNA technology may also be used to remove some or all of the DNA encoding either or both of the light and heavy chains that is not necessary for ST2 binding. The molecules expressed from such truncated DNA molecules are useful in the methods of this disclosure. In addition, bi-functional antibodies may be produced, in which one heavy and one light chain are derived from anti-ST2 antibodies and the other heavy and light chain are specific for an antigen other than ST2, or another epitope of ST2.

Chimeric recombinant anti-ST2 antibodies can be produced by transforming a host cell with a suitable expression vector comprising DNA encoding the desired immunoglobulin light and heavy chains, in which all or some of the DNA encoding the hinge and constant regions of the heavy and/or the light chain have been substituted with DNA from the corresponding region of an immunoglobulin light or heavy chain of a different species. When the original recombinant antibody is nonhuman, and the inhibitor is to be administered to a human, substitution of corresponding human sequences is preferred. An exemplary chimeric recombinant antibody has mouse variable regions and human hinge and constant regions. See generally, U.S. Pat. No. 4,816,397; Morrison et al., "Chimeric Human Antibody Molecules: Mouse Antigen-Binding Domains With Human Constant Region Domains", *Proc. Natl. Acad. Sci. USA,* 81, pp. 6851-55 (1984); Robinson et al., International Patent Publication PCT/US86/02269; Akira, et al, European Patent Application 184,187; Taniguchi, M., European Patent Application 171,496; Neuberger et al., International Application WO 86/01533; Better et al. (1988) *Science* 240:1041-1043; Liu et al. (1987) *PNAS* 84:3439-3443; Liu et al., (1987), *J. Immunol.* 139:3521-3526; Sun et al (1987) *PNAS* 84:214-218; Nishimura et al., (1987), *Canc. Res.* 47:999-1005; Wood et al. (1985) *Nature* 314:446-449; and Shaw et al., (1988), *J. Natl Cancer Inst.* 80:1553-1559.

Humanized recombinant anti-ST2 antibodies can be generated by replacing sequences of the Fv variable region that are not directly involved in antigen binding with equivalent sequences from human Fv variable regions. General methods for generating humanized antibodies are provided by Morrison, S. L., (1985), *Science* 229:1202-1207, by Oi et al., (1986), *BioTechniques* 4:214, and by Queen et al., U.S. Pat. No. 5,585,089, U.S. Pat. No. 5,693,761 and U.S. Pat. No. 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an anti-ST2 antibody. Nucleic acids encoding the humanized antibody, or fragment thereof, can then be cloned into an appropriate expression vector.

Humanized or CDR-grafted antibody molecules or immunoglobulins can be produced by CDR-grafting or CDR substitution, wherein one, two, or all CDRs of an immunoglobulin chain can be replaced. See, e.g., U.S. Pat. No. 5,225,539; Jones et al. (1986) *Nature* 321:552-525; Verhoeyan et al. (1988) *Science* 239:1534; Beidler et al. (1988) *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference. All of the CDRs of a particular human antibody may be replaced with at least a portion of a non-human CDR or only some of the CDRs may be replaced with non-human CDRs. It is only necessary to replace the number of CDRs required for binding of the humanized antibody to a predetermined antigen, e.g., ST2.

Also within the scope of the methods described herein are humanized antibodies, including immunoglobulins, in which specific amino acids have been substituted, deleted or added. In particular, preferred humanized antibodies have amino acid substitutions in the framework region, such as to improve binding to the antigen. For example, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the contents of which are hereby incorporated by reference. Other techniques for humanizing immunoglobulin chains, including antibodies, are described in Padlan et al. EP 519596 A1, published on Dec. 23, 1992.

Human monoclonal antibodies (mAbs) directed against human ST2 can be generated using transgenic mice carrying the complete human immune system rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. (1994) *Nature* 368:856-859; Green, L. L. et al. (1994) *Nature Genet.* 7:13-21; Morrison, S. L. et al. (1994) *Proc. Natl. Acad. Sci. USA* 81:6851-6855; Bruggeman et al. (1993) *Year Immunol* 7:33-40; Tuaillon et al. (1993) *PNAS* 90:3720-3724; Bruggeman et al. (1991) *Eur J Immunol* 21:1323-1326).

Monoclonal antibodies can also be generated by other methods known to those skilled in the art of recombinant DNA technology. An alternative method, referred to as the "combinatorial antibody display" method, has been developed to identify and isolate antibody fragments having a particular antigen specificity, and can be utilized to produce monoclonal antibodies (for descriptions of combinatorial antibody display see e.g., Sastry et al. 1989 *PNAS* 86:5728; Huse et al. (1989) *Science* 246:1275; and Orlandi et al. (1989) *PNAS* 86:3833). After immunizing an animal with an immunogen as described above, the antibody repertoire of the resulting B-cell pool is cloned. Methods are generally known for obtaining the DNA sequence of the variable regions of a diverse population of immunoglobulin molecules by using a mixture of oligomer primers and PCR (Larrick et al., (1991), *Biotechniques* 11:152-156; Larrick et al., (1991), *Methods: Companion to Methods in Enzymology* 2:106-110).

Examples of methods and reagents particularly amenable for use in generating a variegated antibody display library can be found in, for example, Ladner et al U.S. Pat. No. 5,223,409; Kang et al International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffiths et al. (1993) EMBO J 12:725-734; Hawkins et al. (1992) J Mol Biol 226: 889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982. Kits for generating phage display libraries are commercially available (e.g., the Pharmacia Recombinant Phage Antibody System, catalog no. 27-9400-01; and the Stratagene SurfZAP™ phage display kit, catalog no. 240612).

In certain embodiments, the V region domains of heavy and light chains can be expressed on the same polypeptide, joined by a flexible linker to form a single-chain Fv fragment, and the scFV gene subsequently cloned into the desired expression vector or phage genome. As generally described in McCafferty et al., Nature (1990) 348:552-554, complete VH and VL domains of an antibody, joined by a flexible (Gly4-Ser)3 linker can be used to produce a single chain antibody which can render the display package separable based on antigen affinity. Isolated scFV antibodies immunoreactive with the antigen can subsequently be formulated into a pharmaceutical preparation for use in the subject method.

Specific antibodies with high affinities for a surface protein can be made according to methods known to those in the art, e.g., methods involving screening of libraries (Ladner, R. C., et al., U.S. Pat. No. 5,233,409; Ladner, R. C., et al, U.S. Pat. No. 5,403,484). Further, the methods of these libraries can be used in screens to obtain binding determinants that are mimetics of the structural determinants of antibodies. See, for example, Bajorath, J. and S. Sheriff, (1996), Proteins: Struct., Funct., and Genet. 24 (2), 152-157; Webster, D. M. and A. R. Rees, (1995), "Molecular modeling of antibody-combining sites," in S. Paul, Ed., *Methods in Molecular Biol.* 51, Antibody Engineering Protocols, Humana Press, Totowa, N.J., pp 17-49; and Johnson, G., Wu, T. T. and E. A. Kabat, 1995, "Seqhunt: A program to screen aligned nucleotide and amino acid sequences," in *Methods in Molecular Biol.* 51, op. cit., pp 1-15.

Fragments of anti-ST2 antibodies that are not intact antibodies are also useful in the methods described herein. Such fragments can be derived from any of the antibodies described above. For example, antigen-binding fragments or antigen-binding portions, as well as full-length monomeric, dimeric or trimeric polypeptides derived from the above-described antibodies are themselves useful. Useful antigen-binding fragments or antigen-binding portions of this type include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" or "antigen binding portion" of an antibody. These antibody fragments are obtained using conventional techniques known to those with skill in the art, and the fragments are screened for utility in the same manner as are intact antibodies. Anti-ST2 heavy chains are preferred anti-ST2 antibody fragments or proteins.

Antibody fragments can also be produced by chemical methods, e.g., by cleaving an intact antibody with a protease, such as pepsin or papain, and optionally treating the cleaved product with a reducing agent. Alternatively, useful fragments can be produced by using host cells transformed with truncated heavy and/or light chain genes. Heavy and light chain monomers may be produced by treating an intact antibody with a reducing agent, such as dithioreitol, followed by purification to separate the chains. Heavy and light chain monomers may also be produced by host cells transformed with DNA encoding either the desired heavy chain or light chain, but not both. See, e.g., Ward et al., "Binding Activities of a Repertoire of Single Immunoglobulin Variable Domains Secreted from *Escherichia coli*", *Nature*, 341, pp. 544-46 (1989); Sastry et al., "Cloning of the Immunological Repertoire in *Escherichia coli* for Generation of Monoclonal Catalytic Antibodies: Construction of a Heavy Chain Variable Region-Specific cDNA Library", *Proc. Natl. Acad. Sci. USA*, 86, pp. 5728-32 (1989).

ST2 Mimetic or Small Molecule Agents

Also useful in the methods described herein are ST2 mimetic agents. These agents can be peptides, semi-peptidic compounds or non-peptidic compounds (e.g., small organic molecules).

In preferred embodiments, the test agent is a member of a combinatorial library, e.g., a peptide or organic combinatorial library, or a natural product library. In a preferred embodiment, the plurality of test compounds, e.g., library members, includes at least 10, $10^2$, $10^3$, $10^4$, $10^5$, $10^6$, $10^7$, or $10^8$ compounds. In a preferred embodiment, the plurality of test compounds, e.g., library members, share a structural or functional characteristic.

In one embodiment, the disclosure features libraries of ST2 modulators. The synthesis of combinatorial libraries is well known in the art and has been reviewed (see, e.g., E. M. Gordon et al., *J. Med. Chem.* (1994) 37:1385-1401; DeWitt, S. H.; Czarnik, A. W. *Acc. Chem. Res.* (1996) 29:114; Armstrong, R. W.; Combs, A. P.; Tempest, P. A.; Brown, S. D.; Keating, T. A. *Acc. Chem. Res.* (1996) 29:123; Ellman, J. A. *Acc. Chem. Res.* (1996) 29:132; Gordon, E. M.; Gallop, M. A.; Patel, D. V. *Acc. Chem. Res.* (1996) 29:144; Lowe, G. *Chem. Soc. Rev.* (1995) 309, Blondelle et al. *Trends Anal. Chem.* (1995) 14:83; Chen et al. *J. Am. Chem. Soc.* (1994) 116:2661; U.S. Pat. Nos. 5,359,115, 5,362,899, and 5,288,514; PCT Publication Nos. WO92/10092, WO93/09668, WO91/07087, WO93/20242, WO94/08051).

Libraries of compounds for use in the methods described herein can be prepared according to a variety of methods, some of which are known in the art. For example, a "split-pool" strategy can be implemented in the following way: beads of a functionalized polymeric support are placed in a plurality of reaction vessels; a variety of polymeric supports suitable for solid-phase peptide synthesis are known, and some are commercially available (for examples, see, e.g., M. Bodansky "Principles of Peptide Synthesis", 2nd edition, Springer-Verlag, Berlin (1993)). To each aliquot of beads, a solution of a different activated amino acid is added, and the reactions are allowed to proceed to yield a plurality of immobilized amino acids, one in each reaction vessel. The aliquots of derivatized beads are then washed, "pooled" (i.e., recombined), and the pool of beads is again divided, with each aliquot being placed in a separate reaction vessel. Another activated amino acid is then added to each aliquot of beads. The cycle of synthesis is repeated until a desired peptide length is obtained. The amino acid residues added at each synthesis cycle can be randomly selected; alternatively, amino acids can be selected to provide a "biased" library, e.g., a library in which certain portions of the inhibitor are selected non-randomly, e.g., to provide an inhibitor having known structural similarity or homology to a known peptide capable of interacting with an antibody, e.g., the an anti-idiotypic antibody antigen binding site. It will be appreciated that a wide variety of peptidic, peptidomimetic, or non-peptidic compounds can be readily generated in this way.

The "split-pool" strategy results in a library of peptides, e.g., inhibitors that can be used to prepare a library of test compounds that can be potentially used in the methods described herein. In another illustrative synthesis, a "diversomer library" is created by the method of Hobbs DeWitt et al. (*Proc. Natl. Acad. Sci. U.S.A.* 90:6909 (1993)). Other synthesis methods, including the "tea-bag" technique of Houghten (see, e.g., Houghten et al., *Nature* 354:84-86

(1991)) can also be used to synthesize libraries of compounds that can be potentially used in the methods described herein.

Libraries of compounds can be screened to determine whether any members of the library have a desired activity, and, if so, to identify the active species. Methods of screening combinatorial libraries have been described (see, e.g., Gordon et al., *J Med. Chem.*, supra). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, calorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries for compounds that can be used in the methods described herein are described below.

In one embodiment, compounds for use in the methods described herein can be screened for the ability to interact with ST2 polypeptide by assaying the activity of each compound to bind directly to the polypeptide, e.g., by incubating the test compound with an ST2 polypeptide and a lysate, e.g., a T or APC cell lysate, e.g., in one well of a multiwell plate, such as a standard 96-well microtiter plate. In this embodiment, the activity of each individual compound can be determined. A well or wells having no test compound can be used as a control. After incubation, the activity of each test compound can be determined by assaying each well. Thus, the activities of a plurality of test compounds can be determined in parallel.

In still another embodiment, large numbers of test compounds can be simultaneously tested for binding activity. For example, test compounds can be synthesized on solid resin beads in a "one bead-one compound" synthesis; the compounds can be immobilized on the resin support through a photolabile linker. A plurality of beads (e.g., as many as 100,000 beads or more) can then be combined with yeast cells and sprayed into a plurality of "nano-droplets", in which each droplet includes a single bead (and, therefore, a single test compound). Exposure of the nano-droplets to UV light then results in cleavage of the compounds from the beads. It will be appreciated that this assay format allows the screening of large libraries of test compounds in a rapid format.

Combinatorial libraries of compounds can be synthesized with "tags" to encode the identity of each member of the library (see, e.g., W. C. Still et al., U.S. Pat. No. 5,565,324 and PCT Publication Nos. WO 94/08051 and WO 95/28640). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels. Such a tagging scheme can be useful, e.g., in the "nano-droplet" screening assay described above, to identify compounds released from the beads.

In preferred embodiments, the libraries of compounds that can be potentially used in the methods described herein contain at least 30 compounds, more preferably at least 100 compounds, and still more preferably at least 500 compounds. In preferred embodiments, the libraries of compounds contain fewer than $10^9$ compounds, more preferably fewer than $10^8$ compounds, and still more preferably fewer than $10^7$ compounds.

Derivatized Modulators

Also useful in the methods described herein are derivatized modulators, in which, for example, any of the antibodies, soluble ST2 polypeptides, or ST2 mimetic agents described herein are functionally linked (by chemical coupling, genetic fusion or otherwise) to one or more members independently selected from the group consisting of anti-ST2 antibodies, soluble ST2 polypeptides, ST2 mimetic agents, cytotoxic agents and pharmaceutical agents.

One type of derivatized modulator is produced by crosslinking two or more modulators (of the same type or of different types). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Also useful are modulators linked to one or more cytotoxic or pharmaceutical agents. Useful pharmaceutical agents include biologically active peptides, polypeptides and proteins, such as antibodies specific for a human polypeptide other than ST2, or portions thereof Useful pharmaceutical agents and cytotoxic agents also include daunorubicin, *Pseudomonas* exotoxin A, interferon, and nitrogen mustard.

Preferred inhibitors derivatized with a pharmaceutical agent include recombinantly-produced polypeptides in which a soluble ST2 polypeptide, or a peptidyl ST2 mimetic agent is fused to all or part of an immunoglobulin heavy chain hinge region and all or part of a heavy chain constant region. Preferred polypeptides for preparing such fusion proteins are soluble ST2 polypeptides. Most preferred are fusion proteins containing ST2 polypeptides fused to a portion of an immunoglobulin, e.g., the Fc region of immunoglobulin. Such fusion proteins are expected to exhibit prolonged serum half-lives and enable modulator dimerization.

The utility in the methods described herein of specific soluble ST2 polypeptides, anti-ST2 antibodies, or ST2 mimetic agents may easily be determined by assaying e.g., their ability to bind a naturally-occurring ligand of ST2, e.g., IL33, or to bind ST2. The binding characteristics of soluble polypeptides, antibodies and mimetic agents useful in the methods described herein may be assayed in several known ways, such as by radiolabeling the antibody, polypeptide or agent (e.g., $^{35}S$ or $^{125}I$) and then contacting the labeled polypeptide, mimetic agent or antibody with $ST2^+$ cells, as appropriate. Binding characteristics may also be assayed using an appropriate enzymatically-labelled secondary antibody known in the art. Rosetting competition assays such as those described by Seed et al. (*Proc. Natl. Acad. Sci. USA*, 84, pp. 3365-69 (1987)) may also be used.

Antisense

Nucleic acid molecules that are antisense to a nucleotide encoding ST2, e.g., antisense to an ST2 polypeptide, can also be used as an ST2 modulator, e.g., an ST2 inhibitor. An "antisense" nucleic acid includes a nucleotide sequence that is complementary to a "sense" nucleic acid encoding the component, e.g., complementary to the coding strand of a double-stranded cDNA molecule or complementary to an mRNA sequence. Accordingly, an antisense nucleic acid can form hydrogen bonds with a sense nucleic acid. The antisense nucleic acid can be complementary to an entire coding strand, or to only a portion thereof. For example, an antisense nucleic acid molecule which antisense to the "coding region" of the coding strand of a nucleotide sequence encoding the component can be used.

The coding strand sequences encoding ST2 are known. Given the coding strand sequences encoding these proteins, antisense nucleic acids can be designed according to the rules of Watson and Crick base pairing. The antisense nucleic acid molecule can be complementary to the entire coding region of mRNA, but more preferably is an oligonucleotide which is antisense to only a portion of the coding or noncoding region of mRNA. For example, the antisense oligonucleotide can be complementary to the region surrounding the translation start site of the mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest.

RNAi

Double stranded nucleic acid molecules that can silence a gene encoding an ST2 described herein, e.g., sST2, can also be used as an ST2 inhibitor. RNA interference (RNAi) is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human cells, including human embryonic kidney and HeLa cells (see, e.g., Elbashir et al. Nature May 24, 2001;411 (6836):494-8). In one embodiment, gene silencing can be induced in mammalian cells by enforcing endogenous expression of RNA hairpins (see Paddison et al., 2002, PNAS USA 99: 1443-1448). In another embodiment, transfection of small (21-23 nt) dsRNA specifically inhibits gene expression (reviewed in Caplen (2002) Trends in Biotechnology 20:49-51).

Briefly, RNAi is thought to work as follows. dsRNA corresponding to a portion of a gene to be silenced is introduced into a cell. The dsRNA is digested into 21-23 nucleotide siRNAs, or short interfering RNAs. The siRNA duplexes bind to a nuclease complex to form what is known as the RNA-induced silencing complex, or RISC. The RISC targets the homologous transcript by base pairing interactions between one of the siRNA strands and the endogenous mRNA. It then cleaves the mRNA ~12 nucleotides from the 3' terminus of the siRNA (reviewed in Sharp et al (2001) Genes Dev 15: 485-490; and Hammond et al. (2001) Nature Rev Gen 2: 110-119).

RNAi technology in gene silencing utilizes standard molecular biology methods. dsRNA corresponding to the sequence from a target gene to be inactivated can be produced by standard methods, e.g., by simultaneous transcription of both strands of a template DNA (corresponding to the target sequence) with T7 RNA polymerase. Kits for production of dsRNA for use in RNAi are available commercially, e.g., from New England Biolabs, Inc. Methods of transfection of dsRNA or plasmids engineered to make dsRNA are routine in the art.

Gene silencing effects similar to those of RNAi have been reported in mammalian cells with transfection of a mRNA-cDNA hybrid construct (Lin et al., Biochem Biophys Res Commun Mar. 2, 2001; 281(3):639-44), providing yet another strategy for gene silencing.

Therapeutic Applications of RNAi are Described, e.g., in Shuey, Drug Discov Today. Oct. 15, 2002; 7(20):1040-6.

*Combination Therapy*

The agents or modulators described herein, e.g., soluble ST2 polypeptides, can be used in combination with other therapies, e.g., other agents useful in the treatment of lung or liver fibrosis. The other agents are referred to herein as "second agents" or "additional agents" and include one or more of: corticosteroids (e.g., prednisone), cytotoxic drugs (e.g., cyclophosphamide or azathioprine), penicillamine, colchicines, interferon γ, 2-oxoglutarate analogs, prostaglandin analogs, Adefovir and Irbesartan. Such combination therapy can advantageously utilize lower dosages of the therapeutic or prophylactic agents.

Administered "in combination", as used herein, means that two, three, or more, different treatments are delivered to the subject during the course of the subject's affliction with the disorder, e.g., the two or more treatments are delivered after the subject has been diagnosed with the disorder and before the disorder is in remission, or has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. In some embodiments of either case, the treatment is more effective because of combined administration. E.g., the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder, e.g., reduction in liver or lung fibrosis, is greater than what would be observed with one treatment delivered in the absence of the other. The effect of the two treatments can be partially additive, wholly additive, or greater than additive. The delivery can be such that an effect of the first treatment delivered is still detectable when the second is delivered, e.g., when the ST2-modulating agent is delivered first, a reduction in liver or lung fibrosis is still detectable when second agent is delivered. In a preferred embodiment, a delivery of the first treatment and a delivery of the second treatment occur within 1, 2, 5, 10, 15, or 30 days of one another.

In a preferred embodiment, an ST2-modulating agent described herein (e.g., soluble ST2 polypeptide), the second agent (or both), or a pharmaceutical composition containing the same is administered systemically, e.g., intravenously, intramuscularly, subcutaneously, intra-articularly, transdermally, intrathecally, periostally, intratumorally, intralesionally, perilesionally by infusion (e.g., using an infusion device), orally, topically or by inhalation. Preferably, the ST2-modulating agent is administered intramuscularly or intravenously. In other embodiment, the ST2-modulating agent is administered locally, e.g., topically or by needleless injection, to an affected area.

The parenteral administration of an ST2-modulating agent described herein (e.g., soluble ST2 polypeptide), the second agent (or both) or a pharmaceutical composition containing the same can be effected using a needle or a needleless syringe by procedures known in the art. Examples of needleless syringe systems and modes of administration are described in U.S. Pat. No. 6,132,395, U.S. Pat. No. 6,096,002, U.S. Pat. No. 5,993,412, U.S. Pat. No. 5,893,397, U.S. Pat. No. 5,520,639, U.S. Pat. No. 5,503,627, U.S. Pat. No. 5,399,163, U.S. Pat. No. 5,383,851, U.S. Pat. No. 5,312,577, U.S. Pat. No. 5,312,335, the contents of all of which are hereby incorporated by reference.

Pharmaceutical Compositions

Preferably, an effective amount of an ST2-modulating agent described herein (e.g., a soluble ST2 polypeptide or ST2-Fc fusion protein described herein) is administered. By "effective amount" is meant an amount capable of lessening the spread or severity of the conditions described herein. In therapeutic embodiments, an effective amount of the agent refers to an amount of an agent which is effective at inhibiting, relieving, or ameliorating the symptoms of the disorder (e.g., lung or liver fibrosis), or in prolonging the survival of the patient with the disorder beyond that expected in the absence of such treatment. In prophylactic embodiments, an effective amount of an ST2-modulating agent described herein refers to an amount of an agent that is effective in preventing or delaying the occurrence of the onset or recurrence of the disorder, e.g., lung or liver fibrosis.

It will be apparent to those of skill in the art that the effective amount of agent will depend, inter alia, upon the disorder treated (e.g., lung or liver fibrosis resulting from various causes), administration schedule, the unit dose administered, whether the agent is administered in combination with other therapeutic agents, the immune status and health of the patient, the therapeutic or prophylactic activity of the particular agent administered and the serum half-life. Depending on the disorder to be treated, the agent may be packaged differently.

Preferably, a soluble ST2 polypeptide or ST2-Fc fusion protein is administered at a dose between about 0.001 and about 50 mg of the agent per kg body weight, more preferably, between about 0.01 and about 10 mg of the agent per kg body weight, most preferably between about 0.1 and about 4 mg of the agent per kg body weight. IM and IV administration are preferred.

Unit doses are typically administered until an effect is observed. The effect can be measured by a variety of methods, including, lung or liver function assays, or improvement in other affected body areas as may be relevant to the particular disorder. Preferably, the unit dose is administered at regular intervals during a treatment cycle, such as once a week. More preferably, it is administered at regular intervals, e.g., at weekly intervals for an administration period of several weeks, e.g., twelve weeks. More frequent administrations, e.g., two or three times per week are also envisioned and may be adapted if the subject's disorder is severe or if urgent intervention is indicated. Less frequent administrations, e.g., once or twice per month, are also envisioned and may be adopted if the subject responds well to therapy such that maintenance dosing is appropriate. It will be recognized, however, that lower or higher dosages and other administration schedules may be employed during any one particular cycle of administration.

The agent, e.g., ST2 polypeptide or ST2-Fc fusion protein, is also preferably administered in a composition including a pharmaceutically acceptable carrier. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the agent.

Formulations, e.g., pharmaceutical formulations, of an ST2 modulating-agent described herein can be prepared in aqueous or non-aqueous, e.g., lyophilized, forms. Preferred pharmaceutical formulations are suitable for injection. An example of an aqueous formulation encompassed by the present invention includes phosphate buffered saline (PBS) frozen liquid formulation. An example of a lyophilized formulation includes one or more of: citrate, glycine and sucrose. For example, a preferred lyophilized formulation includes 1 to 5% sucrose, preferably 2.5% sucrose, and 0.5% to 2% glycine, preferably 1% glycine, in sodium citrate-citric buffer (at least 10 mM, preferably 25 mM) buffered to a pH of at least about 4, preferably, 5, more preferably 6 (or even more preferably, 6.8).

The second agent may be administered in a single dosage form with an ST2-modulating agent described herein (i.e., as part of the same pharmaceutical composition), a multiple dosage form, separately from the ST2-modulating agent but concurrently, or a multiple dosage form wherein the two components are administered separately and sequentially. Alternatively, the ST2-modulating agent and the other active agent may be in the form of a single conjugated molecule. Conjugation of the two components may be achieved by standard cross-linking techniques well known in the art. A single molecule may also take the form of a recombinant fusion protein. In addition, a pharmaceutical composition useful in the present invention may be used in combination with other therapies described herein. Such combination therapies may advantageously utilize lower dosages of the therapeutic or prophylactic agents.

An ST2-modulating agent described herein, or pharmaceutical composition, can exist in a variety of forms. These include, for example, solid, semi-solid and liquid dosage forms, such as tablets, pills, powders, liquid solutions, dispersions or suspensions, liposomes, suppositories, injectable, infusible, and topical preparations. The preferred form depends on the intended mode of administration and therapeutic application. The preferred forms are injectable or infusible solutions.

Kits

An ST2-modulating agent can be provided in a kit. In one embodiment, the kit includes (a) a container that contains a composition that includes both an ST2-modulating agent (e.g., a soluble ST2 polypeptide) and, optionally (b) informational material. The informational material can be descriptive, instructional, marketing or other material that relates to the methods described herein and/or the use of the agents for therapeutic benefit.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the ST2-modulating agent, e.g., in a suitable amount, manner, or mode of administration (e.g., a dose, dosage form, or mode of administration described herein). The method can be a method of treating fibrosis, as described herein.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about agents therein and/or its use in the methods described herein. Of course, the informational material can also be provided in any combination of formats.

In addition to the ST2-modulating agent, the composition of the kit can include other ingredients, such as a solvent or buffer, a stabilizer, or a preservative. The kit may also include other agents, e.g., a second or third agent, e.g., other therapeutic agents.

The agents can be provided in any form, e.g., liquid, dried or lyophilized form. It is preferred that the agents are substantially pure (although they can be combined together or delivered separate from one another) and/or sterile. When the agents are provided in a liquid solution, the liquid solution preferably is an aqueous solution, with a sterile aqueous solution being preferred. When the agents are provided as a dried form, reconstitution generally is by the addition of a suitable solvent. The solvent, e.g., sterile water or buffer, can optionally be provided in the kit.

The kit can include one or more containers for the composition or compositions containing the agents. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a unit dosage, e.g., a unit that includes the ST2-modulating agent. For example, the kit includes a plurality of syringes, ampules, foil packets, blister packs, or medical devices, e.g., each containing a unit dose. The containers of the kits can be air tight, waterproof (e.g., impermeable to changes in moisture or evaporation), and/or light-tight.

The kit optionally includes a device suitable for administration of the composition, e.g., a syringe or other suitable delivery device. The device can be provided pre-loaded with an ST2-modulating agent, e.g., in a unit dose, or can be empty, but suitable for loading.

Lung Fibrosis

Lung or pulmonary fibrosis is a common feature of many lung diseases, such as idiopathic pulmonary fibrosis, adult respiratory distress syndrome, fibrosis with collagen vascular disease, bronchiolitis obliterans, respiratory bronchiolitis, sarcoidosis, histiocytosis X, Hermansky-Pudlak syndrome, nonspecific interstitial pneumonia, acute interstitial pneumonia, lymphocytic interstitial pneumonia, and cryptogenic organizing pneumonia. Signs or clinical symptoms of lung fibrosis include, e.g., increased deposition of collagen, particularly in alveolar septa and peribronchial parenchyma, thickened alveolar septa, decreased gas exchange resulting in elevated circulating carbon dioxide and reduced circulating oxygen levels, decreased lung elasticity which can manifest as restrictive lung functional impairment with decreased lung volumes and compliance on pulmonary function tests, bilateral reticulonodular images on chest X-ray, progressive dyspnea (difficulty breathing), and hypoxemia at rest that worsens with exercise. Lung fibrosis associated with any of these diseases, or signs or clinical symptoms associated with lung fibrosis, can be treated using the methods described herein.

Liver Fibrosis

Liver or hepatic fibrosis results from damage to the liver and is characterized by accumulation of extracellular matrix proteins. Although the liver has some capacity for the breakdown of extracellular matrix, in some cases fibrosis is not resolved and progressively increases. Liver fibrosis may result in impairment of liver function with the fibrotic material disturbing the organization of the liver, altering blood flow and causing destruction of liver cells. Liver fibrosis may progress to cirrhosis, characterized by nodules of regenerating hepatocytes.

The main causes of liver fibrosis include: pathogens (e.g., hepatitis B, C, or D virus), autoimmune conditions, exposure to a drug, exposure to a chemical, consumption of alcohol, inherited conditions, and primary billiary cirrhosis. Liver fibrosis associated with any of these diseases, or signs or clinical symptoms associated with liver fibrosis, can be treated using the methods described herein.

Selecting Subjects for Treatment

Lung Fibrosis

Subjects that may be treated with agents described herein include subjects with pulmonary fibrosis, particularly early stage pulmonary fibrosis, and subjects at risk of pulmonary fibrosis. Subjects suffering from pulmonary fibrosis include subjects suffering from idiopathic pulmonary fibrosis, sarcoidosis, familial pulmonary fibrosis, pulmonary fibrosis associated with collagen-vascular disorders or vasculitides, histiocytosis X, Goodpasture's syndrome, chronic eosinophilic pneumonia, idiopathic pulmonary hemosiderosis, hypersensitivity pneumonitides; subjects suffering from pulmonary fibrosis caused by inhalation of organic or inorganic dusts, such as coal, crystalline silica and silicates such as asbestos (causing, e.g., silicosis, asbestosis, coal worker's or carbon pneumoconiosis); subjects suffering from pulmonary fibrosis caused by exposure to radiation or toxic agents such as paraquat, caused by an infectious agent, caused by inhalation of noxious gases, aerosols, chemical dusts, fumes or vapors, or drug-induced interstitial lung disease (ILD). Subjects at risk of pulmonary fibrotic disease include subjects undergoing radiation therapy or chemotherapy; subjects with a family history of or genetic factors indicating a predisposition to ILD; subjects in occupations involving exposure to radiation, toxic agents, or inhalation of dusts or noxious vapors; and subjects suffering from infections that may lead to complications that include pulmonary fibrosis. Subjects suffering from pulmonary fibrosis also include subjects suffering from secondary fibrosis, which may be brought on by an inflammatory condition, such as sarcoidosis, rheumatoid arthritis, systemic sclerosis, scleroderma, extrinsic allergic alveolitis, severe asthma, systemic granulomatosis vasculitis and/or adult respiratory distress syndrome (ARDS).

Liver Fibrosis

The subject to be treated can have, be developing, or be at risk of developing liver disease. In particular, the subject has, or is at risk of developing, liver fibrosis. The fibrosis can be at an early stage or may have progressed to a more advanced stage. In some cases, the fibrosis can have progressed to such a stage that the individual has liver cirrhosis. The subject can also display inflammation in regions of the liver and necrotic or degenerating cells can be present in the liver.

The liver of the subject will typically have a buildup of fibrotic extracellular matrix proteins. For example, these can include collagens and in particular type I, II and/or III collagens. Examples of other proteins that can be present in the fibrotic buildup include laminin, fibronectin and proteoglycans.

The liver disease, and in particular the liver fibrosis, in the subject can have a number of possible causes. The fibrosis can be due to infection with a pathogenic organism. For example, the fibrosis can be due to viral infection. In particular, the subject can be infected, or was previously infected, with a virus that causes hepatitis. The subject can have chronic viral hepatitis. The virus may, for example, be hepatitis B, C or D virus. In some cases, and in particular where the subject has viral hepatitis, the subject can also be infected with HIV. It is possible that the subject can be, or was previously, infected with other organisms that cause liver fibrosis and in particular those that are present in the liver during some stage of their life cycle. For example, the subject can have, or previously had, liver fluke.

The subject can have an inherited disease that causes, or increases the risk of, liver disease and in particular of liver fibrosis. For example, the subject can have one or more of hepatic hemochromatosis, Wilson's disease or alpha-1-antitrypsin deficiency. The subject may have an inherited disorder that causes a structural or functional abnormality in the liver that increases the likelihood of liver fibrosis. The subject can be genetically predisposed to develop an autoimmune disorder that damages the liver and hence that can contribute to liver fibrosis.

In some embodiments, the subject to be treated can have liver disease due to a xenobiotic cause. For example, the subject could have been exposed to a chemical, drug or some other agent which causes liver damage and hence fibrosis. The subject could have been exposed to Rezulin®, Serzone® or other drugs thought to cause liver damage and hence potentially liver fibrosis. The subject can be one who has had an overdose of a particular drug or exceeded the recommended dosage of a drug capable of causing liver damage. For example, the subject could have taken an overdose of paracetamol. The subject can be one who has been exposed to chemicals that can cause liver damage such as, for example, at their place of work. For example, the subject could have been exposed to such chemicals in an industrial or agricultural context. The subject could have consumed plants that contain compounds that can cause liver damage, in particular this may be the case where the subject is an animal. For example, the subject could have consumed a plant containing pyrrolizidine alkaloid. The subject could have been exposed to environmental toxins thought to cause liver fibrosis.

The fibrosis may be alcohol-induced. The subject can be, or could have been, an alcoholic. The subject can consume on average more than 50 units of alcohol per week, preferably more than 60 units of alcohol per week, more preferably more than 75 units of alcohol per week and even more preferably more than 100 units of alcohol per week. The subject can be one who has consumed such levels of alcohol for typically more than 5 years, preferably more than 10 years, more preferably more than 15 years and still more preferably for more than 20 years. In cases of alcohol-induced fibrosis the subject can be aged, for example, over 25 years, preferably over 35 years, more preferably over 45 years and even more preferably over 60 years.

In other embodiments, the subject may have one or more of a number of other conditions known to result in liver fibrosis such as, for example, primary biliary cirrhosis, autoimmune chronic active hepatitis, and/or schistosomiasis. The subject can have or could have had, a bile duct blockage. In some cases, the underlying cause of the fibrosis can be unknown. For example, the subject is one diagnosed as having cryptogenic cirrhosis.

Methods for diagnosing liver fibrosis and cirrhosis are well known in the art and in particular to clinicians in the field. Preferably, the subject has been diagnosed as having a liver disease by a medical professional. The subject can display symptoms associated with liver disease such as one or more of: jaundice, skin changes, fluid retention, nail changes, easy bruising, nose bleeds, and male subjects may have enlargement of breasts. The subject can display exhaustion, fatigue, loss of appetite, nausea, weakness and/or weight loss.

The liver disease can be confirmed by physical examination including techniques such as ultrasound. Liver biopsies can be taken to look for buildup of fibrosis, necrotic cells, cellular degeneration and/or inflammation and other characteristic features of liver disease and in particular of liver fibrosis. Liver function can be been assessed in the subject to determine whether this is compromised in the subject. The nature and underlying cause of the liver fibrosis can be characterized. Any history of exposure to causative agents of liver fibrosis can be determined.

Assessing Effectiveness of Treatment

Lung Fibrosis

Lung fibrosis can be assessed in a variety of ways. Lung biopsies can be taken and markers of lung function can be determined. For example, the presence of fibrotic material in the lung can be determined by staining sections from lung biopsies with stains such as Sirius red. The presence and amount of particular fibrotic extracellular matrix components such as, for example, collagens and in particular collagens I and III can be determined. Other methods of assessing lung fibrosis include, e.g., blood gas assays, bronchoscopy, X-ray, or spirometry, all of which are known in the art.

Liver Fibrosis

Whether treatment with an ST2-modulating agent described herein has an effect on liver fibrosis can be assessed in the subject using a number of techniques. Overall improvement in the liver disease from which the subject is suffering can also be assessed. The condition of the subject and liver function in the subject can be assessed. Thus, the subject can be assessed to monitor any lessening in the severity of, or the disappearance altogether, of one or more symptom associated with liver disease and in particular with liver fibrosis. For example, whether or not there is any change in jaundice, fluid retention, ease of bruising, frequency of nose bleeds, skin or nail condition can be determined. The general well-being of the subject can improve and this can be assessed as an indicator of recovery. Thus, subject's increased appetite, reduction in the incidence, or severity of, nausea, increase in weight and/or general feelings of strength and energy can indicate effectiveness of treatment.

The liver function can be assessed in a variety of ways. Liver biopsies or blood samples can be taken and markers of liver function can be determined. Markers of liver function that can be studied include, e.g., hyaluronic acid, procollagen IIIN peptide, procollagen IC peptide, Undulin-collagen 16, 7S type IV collagen, MMP-2 and TIMP-1 levels.

Amount of nodulization, necrosis and/or inflammation in a subject liver can be assessed. The presence of fibrotic material in the liver can be determined by staining sections from liver biopsies with stains such as Sirius red. The presence and amount of particular fibrotic extracellular matrix components such as, for example, collagens and in particular collagens I and III can be determined. Biochemical analyses can also be carried out to determine levels of TIMPs and/or MMPs.

Liver fibrosis can also be measured by analyzing a liver biopsy sample for: (a) necroinflammation (assessed by "grade" as a measure of the severity and ongoing disease activity), and (b) the lesions of fibrosis and parenchymal or vascular remodeling (assessed by "stage" as being reflective of long-term disease progression). See, e.g., Brunt (2000) Hepatol. 31:241-246; and METAVIR (1994) Hepatol. 20:15-20. Based on analysis of the liver biopsy, a score is assigned. A number of standardized scoring systems exist that provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. periportal and/or bridging necrosis; II. intralobular degeneration and focal necrosis; III. portal inflammation; and IV. fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Its scoring system is as follows: stage 0, no fibrosis; stage 1, fibrous expansion of some portal areas, with or without short fibrous septa; stage 2, fibrous expansion of most portal areas, with or without short fibrous septa; stage 3, fibrous expansion of most portal areas with occasional portal to portal (P-P) bridging; stage 4, fibrous expansion of portal areas with marked bridging (P-P) as well as portal-central (P-C); stage 5, marked bridging (P-P and/or P-C) with occasional nodules (incomplete cirrhosis); stage 6, cirrhosis, probable or definite.

The effectiveness of the methods described herein can also be measured and assessed using the Child-Pugh scoring system, which comprises a multicomponent point system based upon abnormalities in serum bilirubin level, serum albumin level, prothrombin time, the presence and severity of ascites, and the presence and severity of encephalopathy. Based on the presence and severity of abnormality of these parameters, patients can be placed in one of three categories of increasing severity of clinical disease: A, B, or C.

In some embodiments, a therapeutically effective amount of an ST2-modulating agent that effects a change of one unit or more in the fibrosis stage, based on pre- and post-therapy liver biopsies, is administered. In some embodiments, a therapeutically effective amount of an ST2-modulating agent reduces liver fibrosis by at least one unit in the METAVIR, the Knodell, the Scheuer, the Ludwig, or the Ishak scoring system.

Secondary, or indirect, indices of liver function can also be used to evaluate the efficacy of treatment with an ST2-modulating agent described herein. Morphometric computerized semi-automated assessment of the quantitative degree of liver fibrosis based upon specific staining of collagen and/or serum markers of liver fibrosis can also be measured as an indication of the efficacy of a subject treatment method. Secondary indices of liver function include, but are not limited to, serum transaminase levels, prothrombin time, bilirubin, platelet count, portal pressure, albumin level, and assessment of the Child-Pugh score. Those skilled in the art can readily measure such indices of liver function, using standard assay methods, many of which are commercially available, and are used routinely in clinical settings.

Serum markers of liver fibrosis can also be measured as an indication of the efficacy of a subject treatment method. Serum markers of liver fibrosis include, but are not limited to, hyaluronate, N-terminal procollagen III peptide, 7S domain of type IV collagen, C-terminal procollagen I peptide, and laminin. Additional biochemical markers of liver fibrosis include: alpha-2-macroglobulin, haptoglobin, gamma globulin, apolipoprotein A, and gamma glutamyl transpeptidase.

Those skilled in the art can readily measure such serum markers of liver fibrosis, using standard assay methods, many of which are commercially available, and are used routinely in clinical settings. Methods of measuring serum markers include immunological-based methods, e.g., enzyme-linked immunosorbent assays (ELISA), radioimmunoassays, and the like, using antibody specific for a given serum marker.

Quantitative tests of functional liver reserve can also be used to assess the efficacy of treatment an ST2-modulating agent described herein. These include: indocyanine green clearance (ICG), galactose elimination capacity (GEC), aminopyrine breath test (ABT), antipyrine clearance, monoethylglycine-xylidide (MEG-X) clearance, and caffeine clearance.

As used here, a "complication associated with cirrhosis of the liver" refers to a disorder that is a sequellae of decompensated liver disease, i.e., occurs subsequently to and as a result of development of liver fibrosis, and includes, but it not limited to, development of ascites, variceal bleeding, portal hypertension, jaundice, progressive liver insufficiency, encephalopathy, hepatocellular carcinoma, liver failure requiring liver transplantation, and liver-related mortality.

Whether treatment with an ST2-modulating agent described herein is effective in reducing the incidence of a disorder associated with cirrhosis of the liver can readily be determined by those skilled in the art.

Reduction in liver fibrosis increases liver function. Some embodiments feature methods for increasing liver function, generally involving administering a therapeutically effective amount of an ST2-modulating agent described herein. Liver functions include, but are not limited to, synthesis of proteins such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism, hormone metabolism, and lipid metabolism; detoxification of exogenous drugs; a hemodynamic function, including splanchnic and portal hemodynamics; and the like.

Whether a liver function is increased is readily ascertainable by those skilled in the art, using well-established tests of liver function. Thus, synthesis of markers of liver function such as albumin, alkaline phosphatase, alanine transaminase, aspartate transaminase, bilirubin, and the like, can be assessed by measuring the level of these markers in the serum, using standard immunological and enzymatic assays. Splanchnic circulation and portal hemodynamics can be measured by portal wedge pressure and/or resistance using standard methods. Metabolic functions can be measured by measuring the level of ammonia in the serum.

Whether serum proteins normally secreted by the liver are in the normal range can be determined by measuring the levels of such proteins, using standard immunological and enzymatic assays. Normal ranges for such serum proteins are known in the art.

The invention is further described in the following examples, which do not limit the scope of the invention described in the claims.

EXAMPLES

Example 1

Mice Treated with an ST2-Fc Fusion Protein Demonstrate Reduced Lung Fibrosis

Methods

Generation of Recombinant Mouse ST2-Fc.

The DNA sequence containing extracellular region of murine ST2L was generated by RT-PCR from the total RNA of BALB-3T3 cells serum-starved for 36 h, followed by stimulation with 10 μg/ml cyclohexamide and 10% serum for 20 h. The RT-PCR reaction was performed using primers: 5'-TGCCATTGCCATAGAGAGAC-3' (forward) and 5'-TAGTAGATGCTTCGGTGATC-3' (reverse) to amplify the region encoding amino acids 1-336 (GenBank Accession Number D13695). The obtained ST2L fragment was linked to a murine IgG2a-Fc fragment, resulting in a nucleic acid sequence encoding an ST2-Fc fusion protein (see FIG. 12B) that was cloned into the CH269 transient expression vector, and used for protein production. The ST2-Fc fusion protein was purified using protein A affinity purification.

The ST2-Fc fusion protein amino acid sequence is depicted in FIG. 12A, where amino acids 1-336 are ST2 sequence, amino acids 337-338 (bold VD) are the translated codons for a restriction site linker (SalI site) used to connect the ST2 to the Fc region and that is not a native sequence to either ST2 or Fc sequence, and amino acids 339-571 are the Fc region of a murine IgG2a. FIG. 12B depicts the nucleotide sequence and shows ST2 nucleotide sequence in lower case followed by the Fc region nucleic acid sequence in upper case. The bold lower case sequence just prior to the upper case is the SalI linker site.

Under anesthesia (100 mg/kg ketamine: 10 mg/kg xylazine, i.p.), the skin of the left flank of a C57BL6 male mouse was shaved and 3 cycles of betadine and isopropanol were applied to cleanse the dorsal skin. An incision was made in the lateral dorsal skin of the mouse using a sterile #15 scalpel. An Alzet® osmotic minipump containing saline, or bleomycin sulfate solution at dosage level of 90 mg/kg (total dose delivered over 7 days) was implanted subcutaneously on Day 0 into male C57BL6 mice. Minipumps delivered saline or bleomycin for 7 days. The mice were dosed i.p. on days −3, 0, 3, 7 and 10 (200 μg/dose) with ST2-Fc. Day 0 represents the start of bleomycin administration.

Lungs were collected on day 28 for histology. Lungs were fixed in situ by intratracheal injection of 1 ml of 10% NBF (Neutral Buffered Formalin), removed from the chest cavity in toto and immersed in formalin for at least 48 hours. Lungs were embedded in paraffin and sections cut tangential to pleural surfaces. Sections were mounted on slides and stained for collagen deposition with Masson's Trichrome stain. The sections were also stained for α-smooth muscle actin. The results were evaluated by light microscopy.

For Masson's Trichrome staining, five micron paraffin sections were deparaffinized and mordanted in Bouin's solution (Rowley Biochemical Institute Inc., Danvers, Mass.) at 56 C for 1 hour. Sections were rinsed in running water, stained with Weigert's Iron Hematoxylin solution (Rowley Biochemical) for 10 minutes, rinsed again in running water and then stained with Biebrich Scarlet Acid Fuchsin solution (Rowley Biochemical) for 2 minutes. Sections were rinsed briefly in distilled water, acidified in Phosphomolybdic-Phosphotungstic Acid solution (Rowley Biochemical) for 15 minutes, and stained with Anilne Blue solution (Rowley Biochemical) for 5 minutes. Differentiation of staining elements was performed using a 1% aqueous solution of glacial acetic acid for five minutes, after which tissue sections were dehydrated to xylene, and coverslips were applied.

Photographs were taken at 100× with a digital camera (Roper Scientific Photometrics Cool Snap fx) and analysis software MetaMorph 6.0.5 was used to analyze the images. Large lung fields from 4 separate animals from each treatment group were analyzed.

Results

Figure 4:
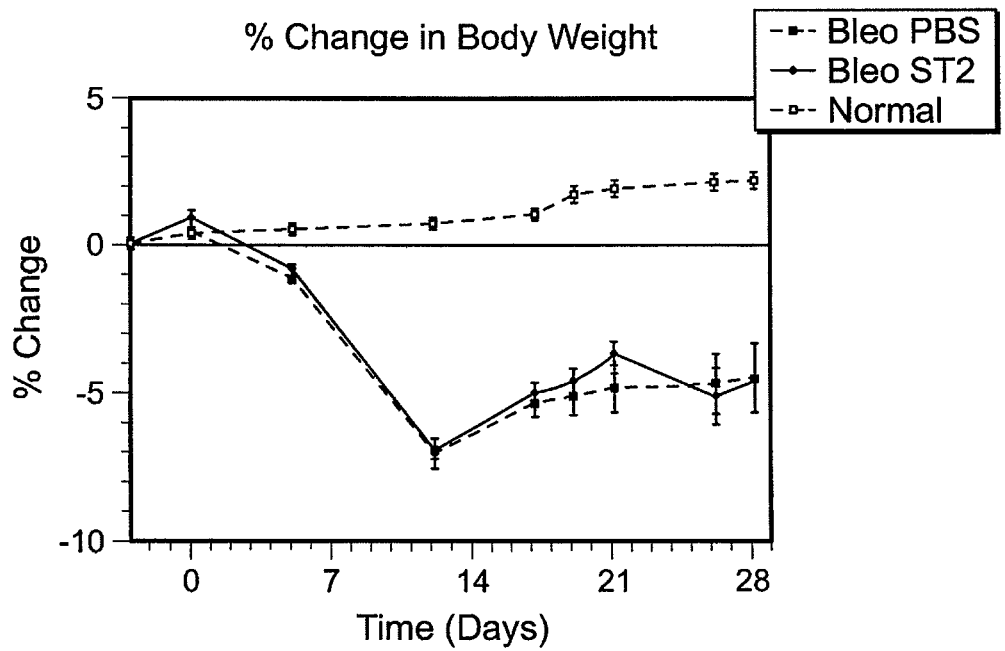
FIG. 4 is a graph of percent change in body weight of mice treated with bleomycin and PBS, bleomycin and ST2-Fc, or control.

Changes in body weight in three groups of mice were monitored: (a) those treated with bleomycin and PBS, (b) those treated with bleomycin and ST2-Fc, and (c) control. FIGS. 1 and 4 show that bleomycin-PBS and bleomycin-ST2 groups of mice lost weight after treatment.

Figure 2:
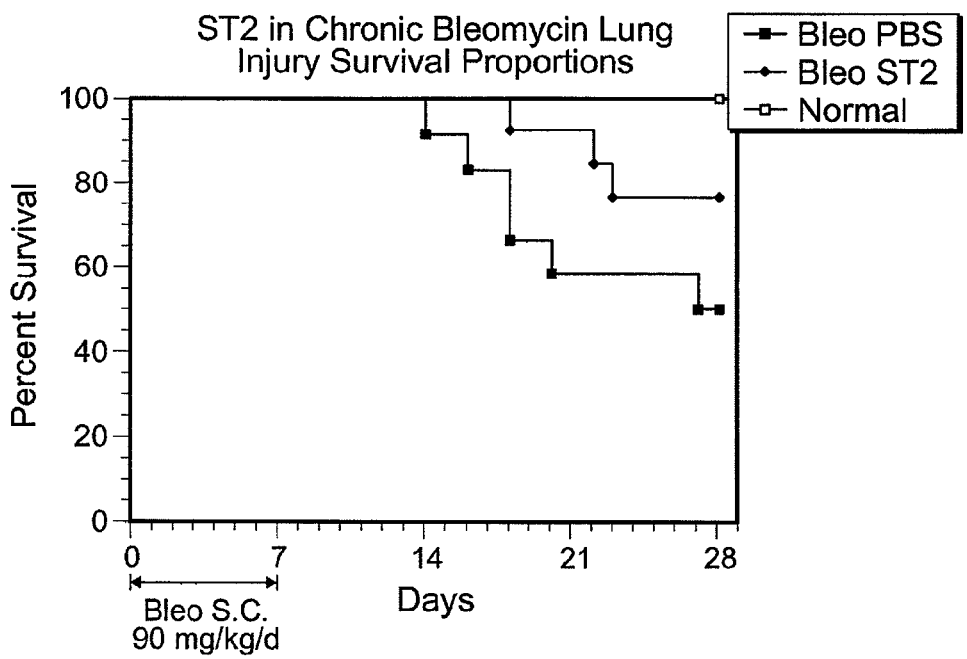
FIG. 2 is a graph of percent survival of mice treated with bleomycin and PBS, bleomycin and ST2-Fc, or control.
Figure 5:
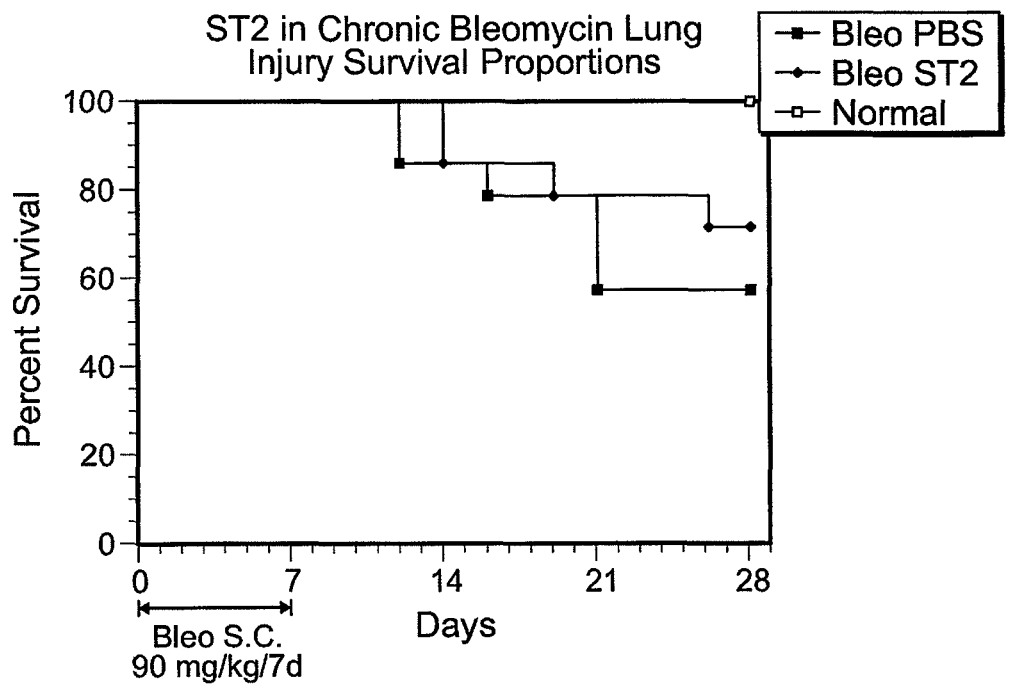
FIG. 5 is a graph of percent survival of mice treated with bleomycin and PBS, bleomycin and ST2-Fc, or control.

The survival of mice treated with bleomycin was compared to the untreated control group. FIGS. 2 and 5 show that treating mice with bleomycin and ST2-Fc increases their survival when compared to the animals treated with bleomycin and PBS.

Figure 3:
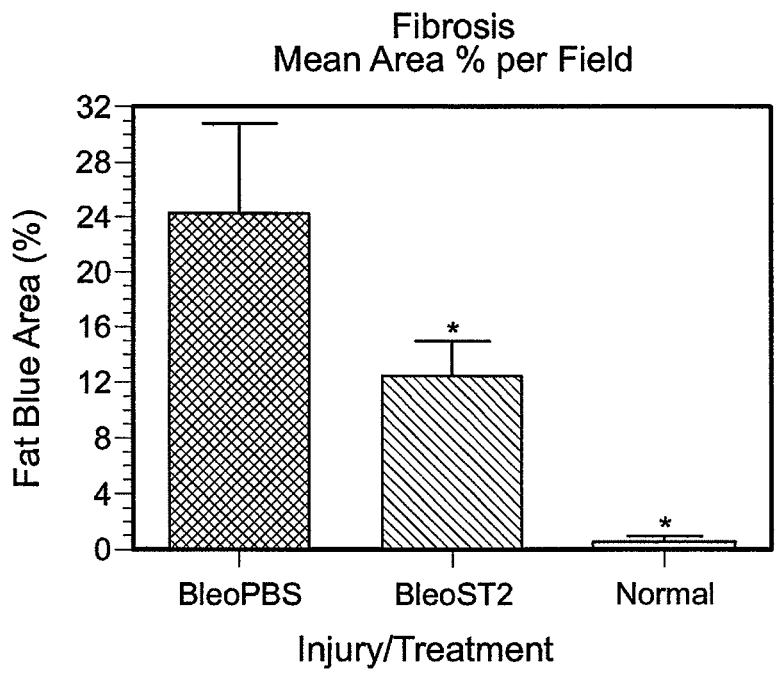
FIG. 3 is a bar graph of the amount of fibrosis in lungs of mice treated with bleomycin and PBS, bleomycin and ST2-Fc, or control.
Figure 6:
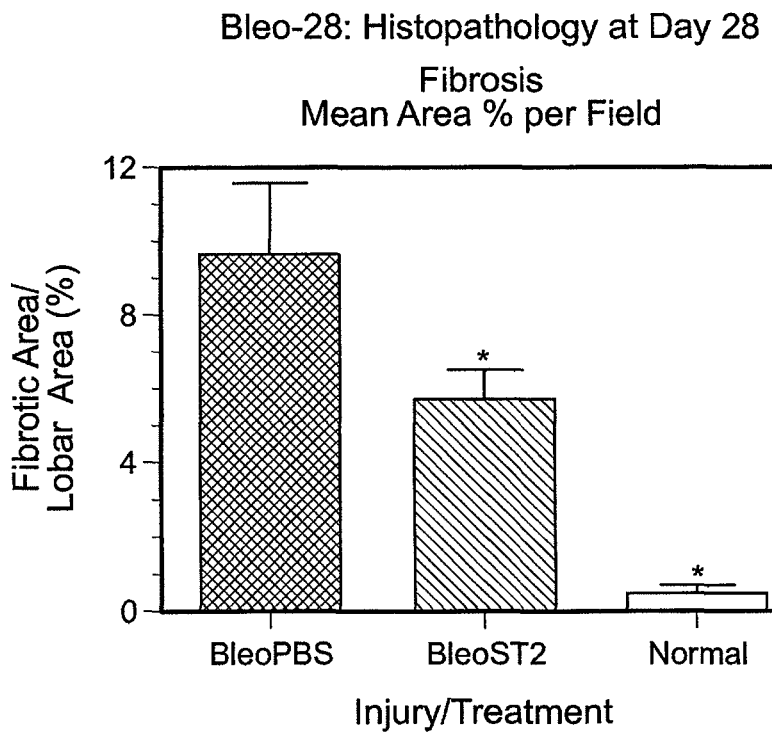
FIG. 6 is a bar graph of the amount of fibrosis in lungs of mice treated with bleomycin and PBS, bleomycin and ST2-Fc, or control.
Figure 7:
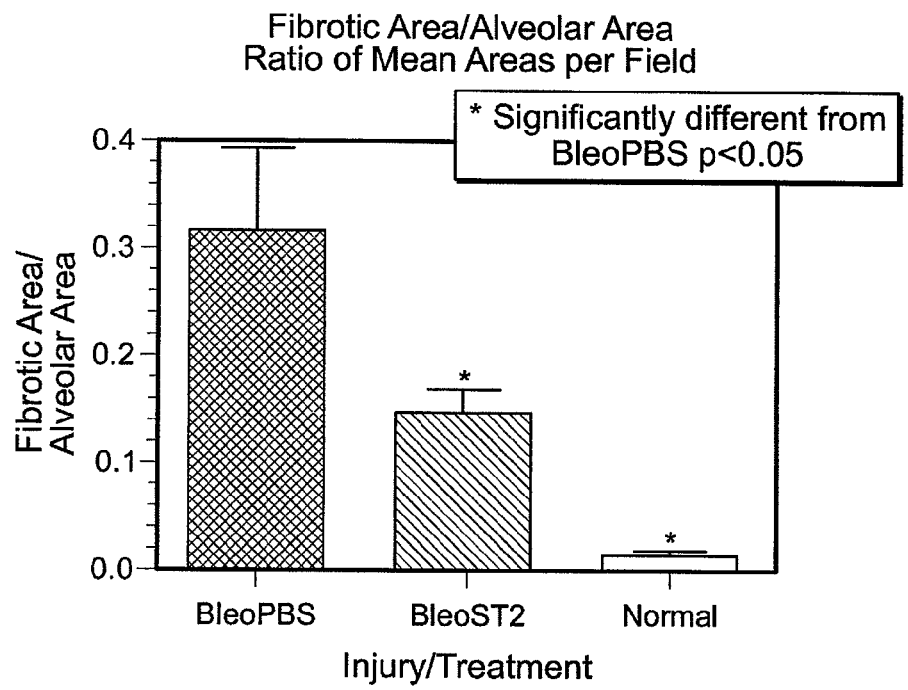
FIG. 7 is a bar graph of fibrotic area/alveolar area ratios in lungs of mice treated with bleomycin and PBS, bleomycin and ST2-Fc, or control.

After staining lung tissue for collagen deposition and smooth muscle actin, the amount of fibrosis in each group was evaluated. FIGS. 3 and 6 show that bleomycin-PBS-treated animals had large areas of collagen/matrix deposition. These areas were reduced by ST2-Fc treatment. Fat blue area in FIG. 3 represents the collagen-staining area of lungs whose thickness is greater than the thickness of the normal alveolar septa. FIG. 7 shows that bleomycin-PBS-treated mice demonstrated large areas of collagen/matrix deposition and reduced alveolar air space. Mice treated with ST2-Fc exhibited decreased collagen/matrix deposition and increased alveolar area. Fibrotic area/lobar area ratios in FIGS. 6 and 7 represent the proportion of the lung lobe that is fibrotic.

Example 2

Recombinant ST2-Fc Favors Type 2 Response by Intrahepatic Lymphocytes in $CCl_4$-Treated Mice Methods Mice.

Male BALB/c wild type (WT), TLR-4 KO, IL-4 KO and IL-4Rα KO mice were purchased from Jackson Laboratory (Bar Harbor, Me.), and $J_H$ KO mice were purchased from Taconic (Germantown, N.Y.). Mice were kept in a specific pathogen-free facility at Biogen Idec. All animal experimentation was approved by Biogen Idec Institutional Animal Care and Use Committee. Mice were 6-8 wks old at the initiation of experiments.

Antibodies and Reagents.

Anti-CD4(RM4-5)-FITC, -PE, -CyChrome, -APC; anti-CD8α (53-6.7)-FITC, -PE, -APC; anti-CD8β(53-5.8)-FITC, -PE, -CyChrome; anti-CD11a (2D7)-FITC, -PE; anti-CD11b (M1/70)-FITC, -PE, -APC; anti-CD16/32(2.4G2)-FITC; anti-CD 18(C71/16)-PE; anti-CD 19(1D3)-FITC, -PE, anti-CD25(PC61)-PE, -APC; anti-CD44(IM7)-FITC, -PE, -CyChrome; anti-CD45RB(16A)-FITC, -PE; anti-CD49a (Ha31/8)-FITC; anti-CD49b (Hal/29)-FITC; anti-CD49b (DX5)-FITC, -PE; anti-CD49d (R1-2)-PE; anti-62L(MEL-14)-FITC, -PE, -APC; anti-CD54(3E2)-PE; anti-CD69 (H1.2F3)-FITC, -PE; anti-CD90.2(53-2.1)-PE; anti-CD103 (M290)-PE; anti-CD122 (5H4)-FITC; anti-CD223 (C9B7W)-PE; anti-Ly-6G(RB6-8C5)-PE, -APC; anti-TCRC$_\beta$ (H57-597)-CyChrome, -APC; and anti-γδTCR (GL3)-FITC, -PE mAbs were purchased from BD Biosciences (San Diego, Calif.). Rat anti-CD4 mAb GK1.5 for in vivo cell depletion and anti-TIM-3(8B.2C12)-PE were purchased from eBioscience (San Diego, Calif.). Mineral oil, $CCl_4$ and collagenase IV were purchased from Sigma (St. Louis, Mo.). Percoll was purchased from Amersham (Uppsala, Sweden). ELISA kits for detection of mouse IL-2, -4, -5, -6, -9, -10, -12, -13, -17, -18, -21, TNFα, IFNγ, and RANTES were purchased from R&D Systems (Minneapolis, Minn.).

Induction of Hepatic Fibrosis and Mouse Treatment.

To induce chronic liver injury, mice were given $CCl_4$ in mineral oil by gavage (1.75 ml/kg) in total volume of 200 µl weekly for 5 or 6 weeks. Control mice were treated with mineral oil only. In acute experiments, mice were sacrificed on days 1, 3 or 5 after single dose of CC14, and in some experiments, one day after the second weekly dose of $CCl_4$ (day 8). Some mice were injected intraperitoneally (i.p.) with 200 µg of ST2-Fc (described in Example 1) or control mouse IgG2a at day −3 relative to the first dose of $CCl_4$, and then twice per week for the duration of $CCl_4$ treatment. In acute experiments, mice were injected with ST2-Fc on day −3 and day 0. Hepatotoxicity was assessed by analysis of alanyltransferase (ALT) levels in sera 24 h after the first dose of $CCl_4$.

Immunohistochemistry.

Three different liver lobes were taken from each mouse and incubated in 4% paraformaldehyde (PFA) in PBS for 2 days prior to embedding for immunohistochemical analysis. General tissue damage was illustrated by haematoxylin and eosin (H&E) staining, and apoptotic areas at early time points by TUNEL staining.

TUNEL staining was performed using an ApopTag In Situ Apoptosis Detection Kit (Chemicon International) according to the manufacturer's instructions. Labeled apoptotic cells were detected using DAB/nickel chloride as the substrate. Slides were counterstained for 5 minutes with methyl green (Vector Laboratories). Hepatic collagen deposition was visualized using Sirius red staining of paraffin embedded liver sections (see Gearge et al., (1999), *PNAS USA* 96:12719-12724).

Kupffer cells and infiltrating macrophages were detected by staining for F4/80. F4/80-specific antibody (clone CI:A3-1, Serotec Inc.) was used at 20 µg/ml. Tissue sections were pretreated with proteinase K (DakoCytomation) for 5 minutes at room temperature. Binding of primary antibody was detected using a Vector Elite ABC kit (Vector Laboratories), using DAB substrate. Slides were counterstained with Mayer's hematoxylin for 1 minute.

Transformed stellate cells were detected by staining for α-smooth muscle actin (αSMA). Antibody specific for αSMA (clone 1A4, DakoCytomation) was used at 1:50 dilution with 30 minutes incubation. Heat-induced epitope retrieval pretreatment of tissue sections was performed in 10 mM citrate buffer, pH 6.0, for 30 seconds at 125° C., kept at 90° C. for 10 seconds, and cooled to room temperature for an additional 20 minutes prior to immunostaining. Binding of primary antibodies to tissue elements was detected using an MM Biotinylation Kit (Biocare Medical), with 3,3'-diaminobenzidine (DAB) substrate. Slides were counterstained with Mayer's hematoxylin for 1 minute.

Interstitial Collagen Quantification.

A total of 3 sections from the liver (each from a different lobe) were stained for each mouse. Black and white pictures of Sirius red staining were made in polarized light at 50× magnification. Tissue occupied the entire area captured by the camera so that total image area was identical in each picture (4-10 pictures per liver). Vasculature normally containing collagen was electronically removed from each image, and the amount of interstitial collagen (white staining) was quantified using MetaMorph image analysis software (Universal Imaging Corp.). Quantification is displayed in arbitrary units (1 correlates to 1000 pixels).

Isolation and In Vitro Culture of Intrahepatic Lymphocytes.

Livers were perfused through the portal vein with PBS, excised, gall bladders removed, the rest of the tissue homogenized in RPMI/5% FBS, centrifuged, resuspended in 0.02% collagenase IV, and incubated for 1 h at 37° C. with constant shaking. Samples were diluted with cold RPMI, hepatocytes were sedimented at 500 rpm for 2.5 min. and discarded. Lymphocytes were purified using discontinuous Percoll gradient 45%/70%, washed in sterile media and used for 4-colour flow cytometric analysis or for in vitro culture with or without anti-CD3ε mAb for 48 h. Supernatants were analyzed for cytokines by ELISA.

Results

Figure 8A:
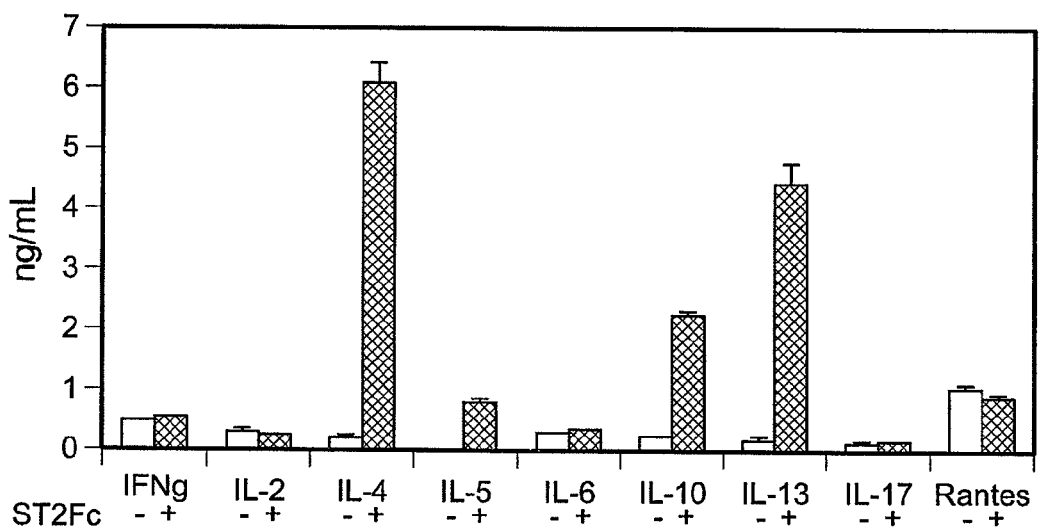
FIG. 8A is a bar graph of production of various cytokines by intrahepatic lymphocytes from $CCl_4$-injured livers of mice treated with ST2-Fc.
Figure 8B:
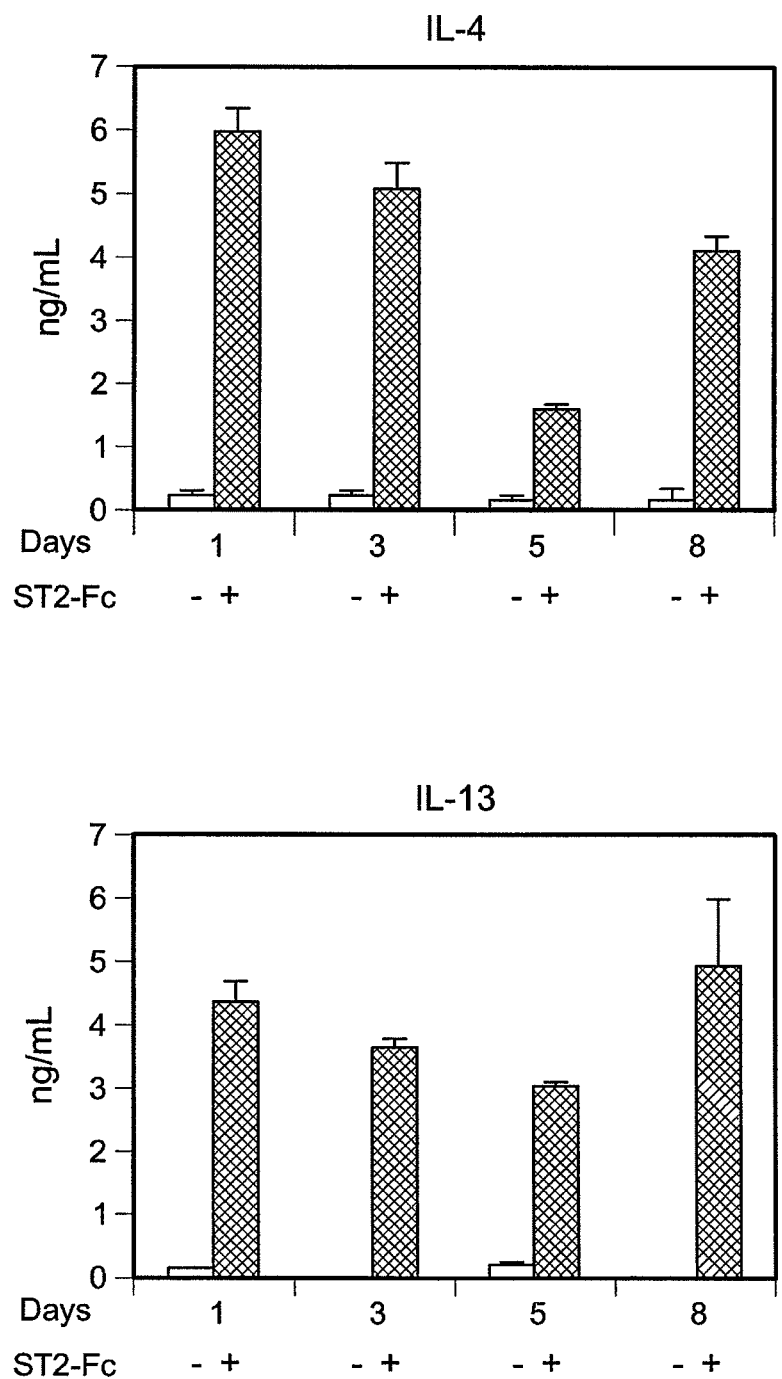
FIG. 8B is a bar graph of the production of IL-4 and IL-13 by intrahepatic lymphocytes from $CCl_4$-injured livers of mice treated with ST2-Fc.
Figure 8C:
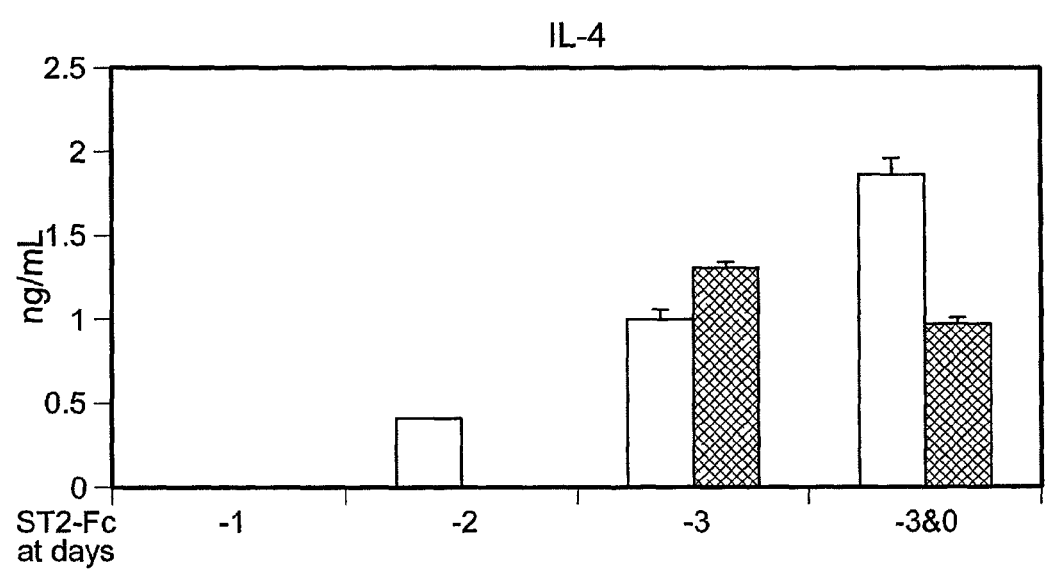
FIG. 8C is a bar graph of IL-4 production by intrahepatic lymphocytes from $CCl_4$-injured livers of mice treated with ST2-Fc at various time points.

To explore the effect of ST2-Fc on an inflammatory liver response, mice gavaged with $CCl_4$ (at 1.75 ml/kg, unless stated otherwise) at days 0 & 7 were injected i.p. with 200 µg soluble ST2-Fc or control mouse IgG at days −3, 0, 3 and 7. Livers harvested from mice sacrificed at days 1, 3, 5 and 8 were used for isolation of intrahepatic lymphocytes (IHL) and for histology studies. IHL were isolated from individual livers and cultured in duplicates. Aliquots of IHL were analyzed by flow cytometry, or stimulated in vitro with anti-CD3ε mAb for 48 h. Supernatants from ex vivo stimulated IHL were screened by ELISA for the presence of Th1 cytokines: IL-2, -12, -17, and IFNγ; Th2 cytokines: IL-4, -5, -9, -10, -13 and -21; and pro-inflammatory cytokines: IL-6, TNFα, and RANTES. Each treatment group contained 4 animals, unless stated otherwise. Samples from control oil or oil+ST2-Fc treated mice, as well as samples cultured without anti-CD3ε did not produce cytokines except for background levels of IL-6 and IL-10, and are not shown. Bars show a mean of quadruplicate values, unless stated otherwise. Error bars show standard deviation. FIGS. 8A-C show that ST2-Fc promotes Th2 response in IHL from $CCl_4$-injured liver. Black bars in FIGS. 8A and 8B represent $CCl_4$+ST2-Fc (200 μg per dose i.p.) treated group and open bars represent $CCl_4$+control IgG treated group. In FIG. 8A, cytokines were measured in IHL samples from mice gavaged by $CCl_4$ on day 0±ST2-Fc injected on days −3 and 0. Measurement for IL-9, IL-12, IL-18, IL-21, and TNFα never yielded any activity above background. A representative experiment out of ten is shown. FIG. 8A shows that $CCl_4$-induced liver injury without ST2-Fc treatment results in a non-polarized response as judged by a modest production of Th1 cytokines (IL-2, -17, IFNγ), Th2 cytokines (IL-4, -10, -13), as well as IL-6 and RANTES. ST2-Fc but not control IgG treatment selectively enhanced secretion of type 2 cytokines IL-4, -5, -10, and -13, but not IL-9 and IL-21 by ex vivo stimulated IHL from $CCl_4$-injured livers (FIG. 8A, and data not shown). These data suggest that exogenous ST2-Fc promotes Th2 response in IHL activated by an ongoing hepatic injury.

The requirement for in vivo activation is corroborated by the observation that since $CCl_4$ inflicted injury at day 0, Th2 enhancing effect of ST2-Fc was fading day 1 through day 5 in spite of ST2-Fc boost at day 4 (see FIG. 8B, showing IL-4 and IL-13 as measured for IHL samples from mice treated with $CCl_4$ on days 0 and 7±ST2-Fc on days −3, 0, 2, 4, and 7, and sacrificed on days 1, 3, 5, and 8. A representative experiment out of four is shown).

A kinetic study showed that enhancement of the Th2 response by IHL isolated one day after $CCl_4$ gavage is observed following a single dose of ST2-Fc on day −3 (relative to gavage) (FIG. 8C). However, delaying ST2-Fc treatment to day −2, −1, or to the day of $CCl_4$ gavage resulted in little if any effect. In FIG. 8C, IL-4 was measured for IHL isolated on day 1 from groups of mice with $CCl_4$ treatment on day 0 combined with and ST2-Fc on day −1, or day −2, or day −3, or days −3 & 0. Black and open bars represent individual mice (two per group) and show a mean from duplicate culture samples. Data from a representative experiment out of two is shown. These data suggest that it takes several days for ST2-Fc to preset conditions needed for Th2 polarization of IHL, but once this milieu is created, polarization occurs within 24 h post-injury.

Example 3

Figure 9:
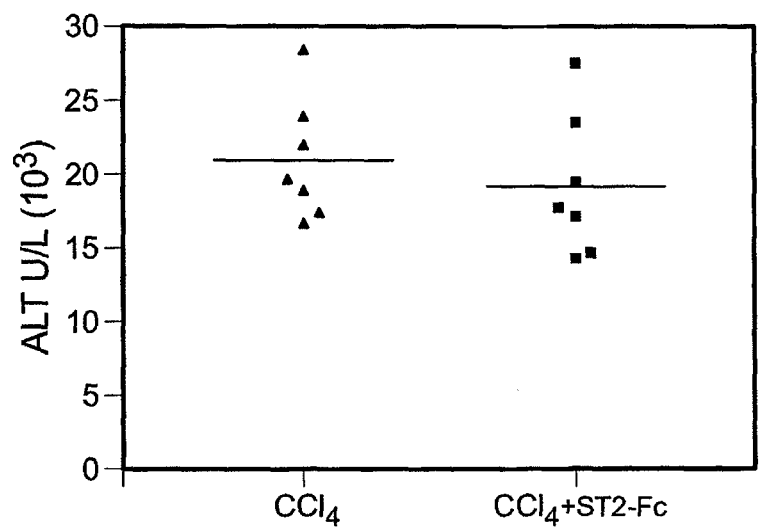
FIG. 9 is a graph of alanyltransferase levels in sera from mice treated with $CCl_4$ and treated with or without ST2-Fc.

Recombinant ST2-Fc Does Not Affect Hepatic Injury, but Accelerates the Onset of Fibrosis in $CCl_4$-Treated Mice Analysis of alanyltransferase activity in sera 24 h post $CCl_4$-induced injury showed no shift in hepatotoxicity of ST2-Fc treated mice (FIG. 9). FIG. 9 shows the effect of ST2-Fc on hepatic injury and repair. Mice were treated with oil (n=2-3), or with oil+ST2-Fc (n=2-3), or with $CCl_4$+ST2-Fc (described in Example 1) (n=3-7), or with $CCl_4$+control IgG (n=3-7). The experiment was performed four times with similar results. $CCl_4$+IgG and $CCl_4$+ST2-Fc groups were bled 24 h after $CCl_4$ gavage, and alanyltransferase (ALT) levels in sera were measured. This observation (of no shift in hepatotoxicity in ST2-Fc treated mice) is in good agreement with TUNEL or H&E staining, both of which failed to reveal a difference in the amount of apoptotic or otherwise damaged cells in liver at day 1. Magnification for representative sections for apoptotic cell-specific TUNEL was performed at day 1. Immunohistochemical staining for F4/80 at days 1-8 post injury showed no significant difference in numbers or distribution of Kupffer cells (a potential source of TGFβ) in injured livers of $CCl_4$/ST2-Fc treated as compared to $CCl_4$-treated mice. Nevertheless, staining for α smooth muscle actin showed more activated myofibroblasts (collagen producing cells) in ST2-Fc exposed injured livers by day 5.

In accordance with those results, at day 8, Sirius red staining revealed a significant increase in the level of collagen deposition of ST2-Fc treated livers. Liver sections were prepared on day 8 from oil, $CCl_4$+control IgG, or $CCl_4$+ST2-Fc treated mice. Oil or $CCl_4$ was given by gavage at days 0 and 7, ST2-Fc or IgG, at days −3, 0, 2, 4, and 7. Each group contained 3 mice. The experiment was performed twice with similar results. Collagen-specific Sirius red staining was performed to visualize interstitial collagen deposition. Together with the in vitro data, this suggests that ST2-Fc treatment does not affect early hepatic injury induced by $CCL_4$, but rather enhances Th2 response to accelerate hepatic fibrosis.

Example 4

Figure 10:
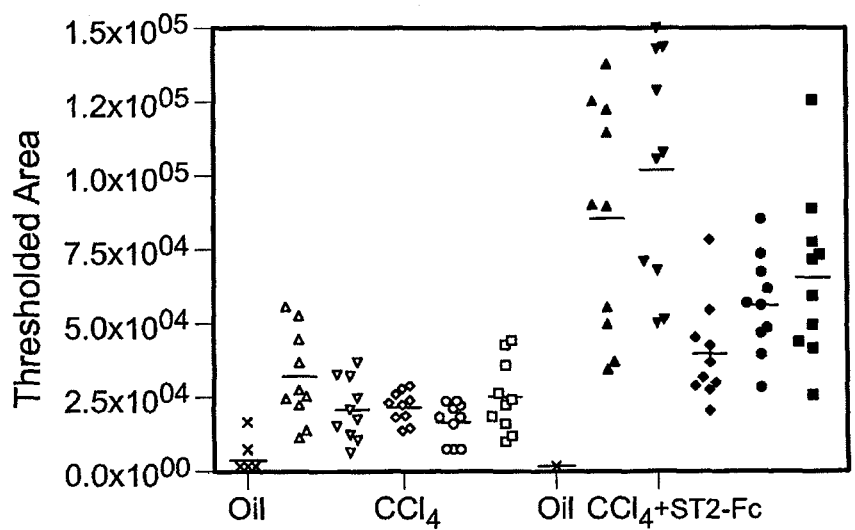
FIG. 10 is a graphical representation of collagen deposition in control mice, mice treated with $CCl_4$, or mice treated with $CCl_4$ and ST2-Fc, as measured by Sirius red staining of liver sections.

Recombinant ST2-Fc Maintains Th2 Commitment and Enhances Collagen Deposition in Chronically-Injured Liver Assessment of whether ST2-Fc-enhanced Th2 response can be maintained in chronically-injured liver to accelerate fibrosis, as measured by increased levels of collagen deposition, was carried out. Mice were treated for 5 weeks with weekly doses of oil (0.2 ml) or $CCl_4$ (1.75 ml/kg) in combination with biweekly doses of control IgG or ST2-Fc (described in Example 1) (200 μg). One week after the fifth weekly gavage with $CCl_4$ or oil mice were sacrificed and collagen-specific Sirius red staining of liver sections was performed to quantify interstitial collagen deposition. At the termination of experiment, ex vivo stimulated IHL from $CCl_4$/ST2-Fc treated but not from $CCl_4$/IgG treated mice demonstrated an exaggerated Th2 response, similar to that seen during the first week of treatment. Sirius red staining revealed a profound increase in the amount of fibrillar collagen depositions in the livers of the ST2-Fc treated mice compared to livers of a control group of mice (FIG. 10; quantification of stained collagen was performed using MetaMorph image analysis software. A column of dots represents a series of sections from one mouse. Mean values are depicted as bars).

Example 5

$CD4^+$-Cells are Required for ST2-Fc Induced Type 2 Response and Fibrosis in $CCl_4$-Injured Liver Extensive 4-colour flow cytometry analyses of the IHL isolated from $CCl_4$ injured livers were performed. Major T cell subsets ($αβTCR^-CD4^+$, $αβTCR^+CD8α^+β^+$, $αβTCR^+CD8α^+β^-$, $αβTCR^+CD4^-CD8α^-$, $γδTCR^+CD8α^+$, and $γδTCR^-CD8α^-$) were analyzed for the expression of major T cell coreceptors (CD2, CD5, CD28, and CD90), activation markers (CD25, CD44, CD54, CD62L, CD69, and CD223), and integrins/differentiation markers (CD11a, CD18, CD29, CD49a, CD49b, CD49d, β7, CD103, CD16/32, CD122, and TIM-3). Additional analysis included IH B cells, macrophages/Kupffer cells, and granulocytes. No significant differences in IHL composition were revealed as a result of treatment with ST2-Fc at early time points, or after 5 weeks of treatment.

Figure 11A:
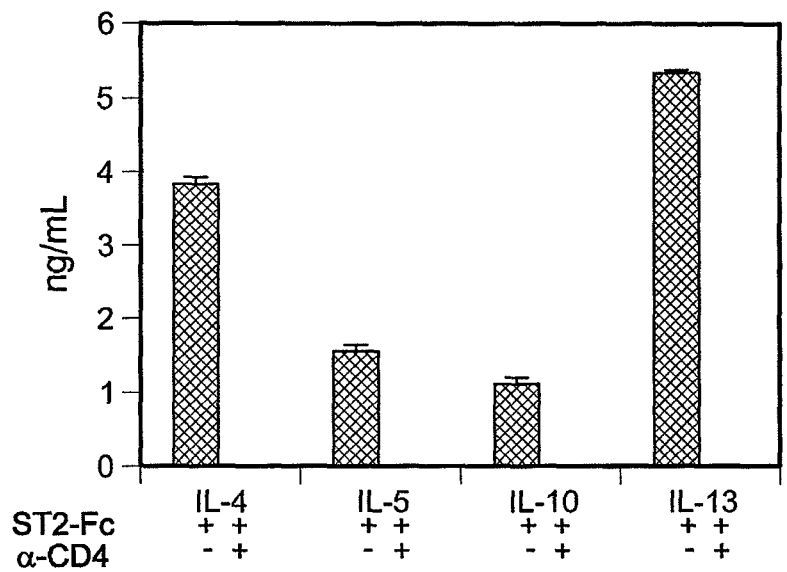
FIG. 11A is a graph of production of various cytokines by ex vivo intrahepatic lymphocytes treated with or without anti-CD4 antibody and treated with ST2-Fc.

To address the cellular source of type 2 cytokines, a depleting anti-CD4 monoclonal antibody was used to render wild type BALB/c mice CD4+ T cell deficient. Mice were injected i.p. with 100 μg of a depleting anti-CD4 antibody or with a control rat IgG on days −5, −3, and 0, were gavaged with 1.75 ml/kg of CCl$_4$ on days 0 and 7, and were injected with 200 μg ST2-Fc or control murine IgG on days −3, 0, 3 and 7. Administration of anti-CD4 at days −5, −3, and 0 eliminated 93-97% of CD4+ cells in spleen and liver, and completely abrogated IL-4, -5, -10 and -13 secretion by IHL from the CCl$_4$/ST2-Fc treated group (FIG. 11A, showing secretion of IL-4, IL-5, IL-10, and IL-13 by ex vivo stimulated IHL harvested at day 1. FIG. 11A shows data from a representative experiment of three. Bars show a mean of triplicate values, error bars show standard deviation).

Figure 11B:
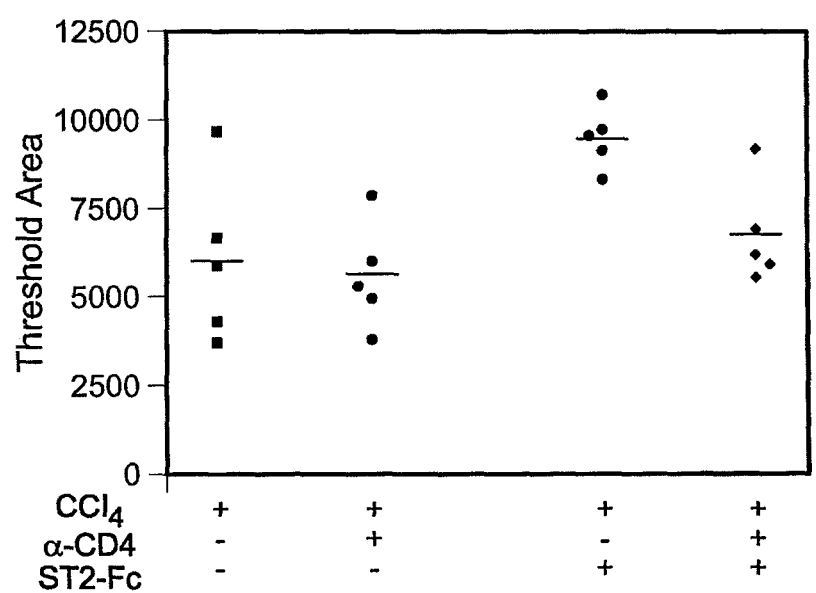
FIG. 11B is a graphical representation of collagen deposition in $CCl_4$-injured livers of control mice, mice treated with anti-CD4 antibody, mice treated with ST2-Fc and mice treated with anti-CD4 antibody and ST2-Fc, as measured by Sirius red staining of liver sections.

Furthermore, staining hepatic tissue for collagen at day 8 post-injury demonstrated that CD4− T cell depletion eliminated the accelerated fibrosis caused by ST2-Fc treatment (FIG. 11B; a column of dots on the collagen quantification graph in represents a treatment group, with each dot representing an individual mouse. Mean values are depicted as bars). These results indicate that the CD4+ T lymphocyte compartment of IH is both the major factor of accelerated fibrogenesis and an important source of type 2 cytokines induced by ST2-Fc in injured liver, and suggests that it is through their Th2 cytokine response that CD4+ IH T lymphocytes enhance hepatic fibrosis.

Example 6

Profibrotic Activity of ST2-Fc is Driven by Th2 Cytokines in TLR-4-Mediated Liver Inflammation To find out whether enhanced Th2 cytokine production was indeed a trigger of fibrogenesis, or instead a side effect of ST2-Fc treatment, the effect of CCL$_4$ or CCl$_4$/ST2-Fc treatment on IL-4Rα KO mice was determined. The IL-4Rα subunit is shared by IL-4 and IL-13 receptor, and as a result IL-4Rα KO mice lack both IL-4 and IL-13 signaling. IL-4Rα KO and WT Balb/c mice were gavaged with oil or with 1.75 ml/kg of CCl$_4$ on days 0 and 7, and injected i.p. with 200 μg of control IgG or ST2-Fc on days −3, 0, 3 and 7, and were sacrificed on day 8. The experiment was performed three times with similar results. Liver sections were stained for interstitial collagen with Sirius red. An accelerated hepatic collagen deposition caused by ST2-Fc by day 8 post-injury was significantly attenuated in IL-4Rα KO livers. Thus, the ability of ST2-Fc to trigger hepatic fibrosis in injured liver was mediated by Th2 cytokines.

Since ST2 activity was attributed to its ability to modulate TLR-2, -4 and -9 signaling, and TLR-4 engagement was shown to tolerize against subsequent CCl$_4$-induced liver injury, the importance of TLR-4 in CCl$_4$-triggered inflammation was analyzed. To address this question, ST2-Fc was administered to TLR-4-deficient CCl$_4$-gavaged BALB/c mice. In contrast to WT mice, in the absence of TLR-4, IHL from both CCl$_4$-treated and CCl$_4$/ST2-Fc treated mice could not be stimulated ex vivo to mount a cytokine response. These data point to TLR-4 as an indispensable mediator of acute inflammation in CCl$_4$-injured liver.

Other embodiments are within a scope of the following claims:

What is claimed is:

1. A method of treating lung fibrosis in a subject, the method comprising administering to the subject a soluble ST2 polypeptide, or a fragment comprising amino acids 1-336 of SEQ ID NO: 2, in an amount effective to treat lung fibrosis.

2. The method of claim 1, wherein the soluble ST2 polypeptide is an ST2 fusion protein.

3. The method of claim 2, wherein the fusion protein is an ST2-Fc fusion protein.

4. The method of claim 1, wherein the subject is a human.

5. The method of claim 1, wherein the soluble ST2 polypeptide is administered intramuscularly.

6. The method of claim 1, wherein the soluble ST2 polypeptide is administered intravenously.

7. The method of claim 1, wherein the soluble ST2 polypeptide is administered at a unit dosage ranging from 2 to 30 mg.

8. The method of claim 1, further comprising evaluating the subject for effectiveness of treatment.

9. A method of treating lung fibrosis in a subject, the method comprising:
   identifying a subject in need of treatment for lung fibrosis, and
   administering a soluble ST2 polypeptide to the subject.

10. The method of claim 9, wherein the soluble ST2 polypeptide is an ST2-Fc fusion protein.

11. A method of treating lung fibrosis in a subject, the method comprising administering to the subject an ST2 fragment comprising an amino acid sequence that is amino acids 1-336 of SEQ ID NO: 2.

\* \* \* \* \*